(12) United States Patent
Eastham et al.

(10) Patent No.: US 9,816,115 B2
(45) Date of Patent: Nov. 14, 2017

(54) PROCESS FOR THE PRODUCTION OF METHYL METHACRYLATE

(71) Applicant: Lucite International UK Limited, Southampton, Hampshire (GB)

(72) Inventors: Graham Ronald Eastham, Redcar (GB); David William Johnson, Redcar (GB); Adrianus Johannes Jozef Straathof, LG Delft (NL); Marco Wilhemus Fraaije, AG Groningen (NL); Remko Tsjibbe Winter, AG Groningen (NL)

(73) Assignee: LUCITE INTERNATIONAL UK LIMITED, Southhampton (GB)

( * ) Notice: Subject to any disclaimer, the term of this patent is extended or adjusted under 35 U.S.C. 154(b) by 251 days.

(21) Appl. No.: 14/403,962

(22) PCT Filed: May 24, 2013

(86) PCT No.: PCT/GB2013/051376
§ 371 (c)(1),
(2) Date: Nov. 25, 2014

(87) PCT Pub. No.: WO2013/179005
PCT Pub. Date: Dec. 5, 2013

(65) Prior Publication Data
US 2015/0112037 A1 Apr. 23, 2015

(30) Foreign Application Priority Data
May 28, 2012 (GB) .................................. 1209425.6

(51) Int. Cl.
C12P 7/62 (2006.01)
C12N 9/02 (2006.01)
C07C 67/343 (2006.01)
C08F 220/10 (2006.01)

(52) U.S. Cl.
CPC .............. *C12P 7/62* (2013.01); *C07C 67/343* (2013.01); *C08F 220/10* (2013.01); *C12N 9/0073* (2013.01); *C12Y 114/13022* (2013.01); *C12Y 114/13084* (2013.01); *C12Y 114/13092* (2013.01)

(58) Field of Classification Search
CPC ....................................................... C12P 7/62
See application file for complete search history.

(56) References Cited

U.S. PATENT DOCUMENTS

| | | | |
|---|---|---|---|
| 4,336,403 A | 6/1982 | Merger et al. | |
| 5,753,474 A | 5/1998 | Ramey | |
| 8,119,844 B2 | 2/2012 | Forster et al. | |
| 2009/0105366 A1 | 4/2009 | Vogt et al. | |
| 2011/0207191 A1 | 8/2011 | Um et al. | |
| 2011/0301316 A1 | 12/2011 | Dubois | |
| 2012/0045807 A1 | 2/2012 | Simpson et al. | |

FOREIGN PATENT DOCUMENTS

| | | |
|---|---|---|
| EP | 0 430 406 B1 | 5/1996 |
| GB | 1 428 277 | 3/1976 |
| WO | WO 00/09682 A1 | 2/2000 |
| WO | WO 03/020890 A2 | 3/2003 |
| WO | WO 2004/007750 A2 | 1/2004 |
| WO | WO 2007/130521 A2 | 11/2007 |
| WO | WO 2007/146377 A1 | 12/2007 |
| WO | 2008/022627 A2 | 2/2008 |
| WO | WO 2008/022627 A2 | 2/2008 |
| WO | WO 2011/077140 A2 | 6/2011 |
| WO | WO 2012/135789 A2 | 10/2012 |
| WO | 2011/077140 A2 | 11/2014 |

OTHER PUBLICATIONS

Eubanks et al. Journal of Bacteriology 1974, 120, 1133-1143.*
Kamerbeek et al. Applied Environmental Microbiology 2003, 69, 419-426.*
Van Beck et al., Chemical Communications, 2012, abstract provided—full document not available, Issue 27, Medline Journal Home Communication.
March's Advanced Organic Chemistry: Reactions, Mechanisms and Structure 6th Edition, p. 1691, 2006.
Torres Pazmino et al., ChemoBioChem, 10:2595-2598, Nov. 2, 2009, pp. 2595-2598, vol. 10, Issue 16, abstract provided—full document not available.
Simpson et al., Journal of Molecular Catalysis B Enzyme 16,, Dec. 5, 2001, pp. 101-108, vol. 16, Issue 2, abstract provided—full document not available.
H. Biebl, Journal of Industrial Microbiology and Biotechnology, 2001, 27, pp. 18-26, vol. 27, Issue 1, abstract provided—full document not available.
R.B. Hespell, Fermentation of Xylan, Corn Fiber, or Sugars to Acetoin and Butanediol by Bacillus Polymyxa Strains, Current Microbiology, 1996, pp. 291-296, vol. 32, Issue 5, abstract provided—full document not available.
Dobrogosz et al., Oxidative Metabolism in *Pediococcus pentosaceus* I., Journal of Bacteriology, 1962, pp. 716-723, vol. 84, No. 4, abstract provided—full document not available.
EPO Written Opinion for PCT/GB2013/051376, 2013.
GB Search Report for GB1209425.6 dated Jul. 24, 2013.
Hannes Leisch et al., Baeyer-Villiger Monooxygenases: More Than Just Green Chemistry, Chemical Reviews, Jul. 2011, pp. 4165-4222, vol. 11, No. 7, Montreal, Canada.
International Search Report for PCT/GB2013/051376 dated Sep. 4, 2013.
Kirschner et al.: "Kinetic Resolution of 4-Hydroxy-2-ketones Catalyzed by a Baeyer-Villiger Monoosygenase"; 2006 Wiley-VCH Verlag GmbH & Co,, KGaA, Weinheim; 4 pages.

(Continued)

*Primary Examiner* — Matthew Coughlin
(74) *Attorney, Agent, or Firm* — Shumaker, Loop & Kendrick, LLP

(57) ABSTRACT

The invention includes a process of producing methyl methacrylate or derivatives thereof is described. The process includes the steps of converting 2-butanone to methyl propionate using a Baeyer-Villiger monooxygenase, and treating the methyl propionate produced to obtain methyl methacrylate or derivatives thereof. A method of preparing polymers or copolymers of methyl methacrylate or its derivatives is also described.

28 Claims, 1 Drawing Sheet

(56) References Cited

OTHER PUBLICATIONS

Zambianchi et al.: Effect of substrate concentration on the enantioselectivity of cyclohexanone monooxygenase from Acinetobacter calcoaceticus and its rationalization; 2000 Elsevier Science Ltd,; 6 pages.
Leisch et al.: "Bayer-Villiger Monooxygenases: More Than Just Green Chemistry"; dx.doi.org/10.1021/cr1003437; Chem. Rev. 2011; pp. 4165-4222.
International Search Report of corresponding International Application No. PCT/GB2013/051376; dated Aug. 27, 2013; 4 pages.
Examination Report for New Zealand IP No. 703172 dated Oct. 5, 2015.

\* cited by examiner

Conversion of different concentrations of 2-butanone by 5 µM CHMO. Each reaction in 1 mL 50 mM Tris-HCl, pH 7.5, containing 100 uM NADPH and 10 mM $Na_2HPO_3$ at room temperature for 24 hours.
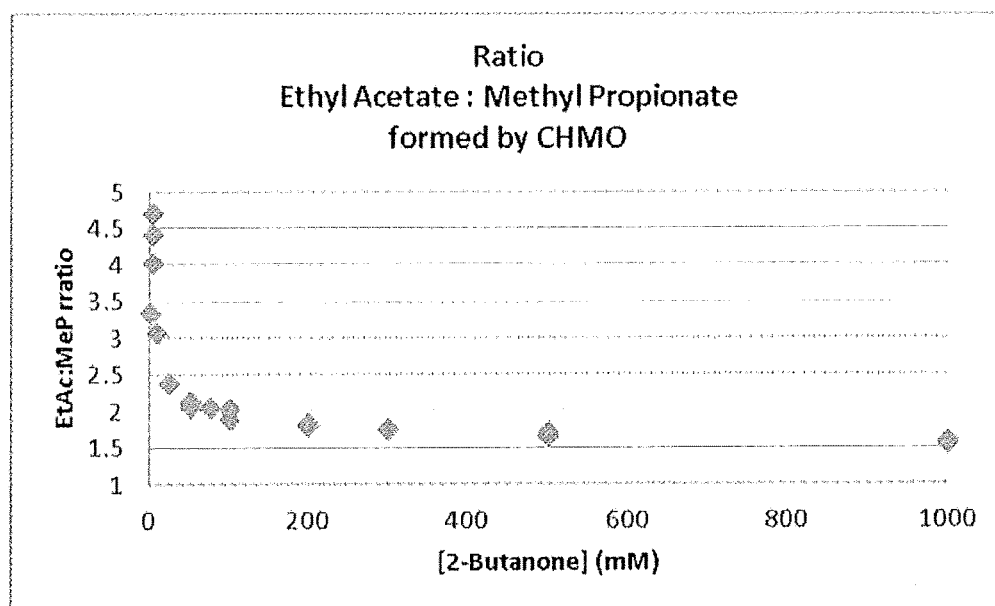

PROCESS FOR THE PRODUCTION OF METHYL METHACRYLATE

CROSS REFERENCE TO RELATED APPLICATIONS

This application is a U.S. National Stage application that claims the benefit of co-pending International Application No. PCT/GB2013/051376, filed on May 24, 2013. Both this application and the aforementioned PCT application also claim priority to GB Application No. 1209425.6, filed on May 28, 2012.

TECHNICAL FIELD AND BACKGROUND OF THE INVENTION

The present invention relates to a process for production of methyl methacrylate or derivatives thereof from 2-butanone by the use of a novel enzyme catalysed process, and polymers and copolymers produced therefrom.
Methacrylic acid (MAA) and its methyl ester, methyl methacrylate (MMA) are important monomers in the chemical industry. Their main application is in the production of plastics for various applications. The most significant polymerisation application is the casting, moulding or extrusion of polymethyl methacrylate (PMMA) to produce high optical clarity plastics. In addition, many copolymers are used, important copolymers are copolymers of methyl methacrylate with α-methyl styrene, ethyl acrylate and butyl acrylate. Furthermore, by a simple transesterification reaction, MMA may be converted to other esters such as butyl methacrylate, lauryl methacrylate etc.

Currently MMA (and MAA) is produced by a number of chemical procedures, one of which is the successful 'Alpha process' whereby MMA is obtained from the ester methyl propionate by anhydrous reaction with formaldehyde. In the Alpha process, the methyl propionate is produced by the carbonylation of ethylene. This ethylene feedstock is derived from fossil fuels. Recently, it has become desirable to also source sustainable biomass feedstocks for the chemical industry. Accordingly, an alternative biomass source for methyl propionate for use in the alpha process would be advantageous.

SUMMARY OF THE INVENTION

Therefore it is one object of the present invention to solve the aforementioned problem, and provide a biological or part biological process for the production of MMA
Surprisingly, the present inventors have found a way to apply unusual enzymes in a novel process to form MMA at an industrially applicable level, thereby providing a new and viable bio-based route to a key monomer.

According to a first aspect of the present invention there is provided a process of producing methyl methacrylate or derivatives thereof comprising the steps of;
(i) converting 2-butanone to methyl propionate using a Baeyer-Villiger monooxygenase, and
(ii) treating the methyl propionate produced to obtain methyl methacrylate or derivatives thereof. The above process may further comprise the step of formation of 2-butanone from raw feedstocks, wherein the term 'raw feedstocks' includes any base organic chemical capable of being transformed into 2-butanone, such as, but not limited to; 2-butanol, acetoin, 2,3-butandiol, or methylvinylketone.

The above process may further comprise the step of fermentation of sugars and/or glycerol and/or microbe convertible gases (such as gases rich in CO and/or $CO_2$) to produce raw feedstocks, wherein the term 'raw feedstocks' is as defined hereinbefore. Suitable sources of microbe convertible gases include industrial flue gases, syngas and reformed methane.

The above process may further comprise the step of obtaining sugars and/or glycerol and/or microbe convertible gases from biomass, wherein the term 'biomass' is defined herein as plant or animal matter either alive or previously alive and it may be considered to be waste matter or matter intended for the use as described in the present invention.

Methyl propionate is preferably treated to produce methyl methacrylate or derivatives thereof by any suitable known chemical or biochemical process. Preferably the methyl propionate is treated to produce methyl methacrylate or methacrylic acid by reaction with formaldehyde or a suitable source thereof in the presence of a suitable catalyst. Typically, this reaction takes place under anhydrous conditions.

A suitable process for preparing the methacrylic acids or ester comprises contacting methyl propionate with a suitable source of formaldehyde of formula I as defined below:

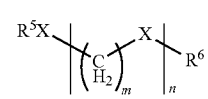

where $R^5$ and $R^6$ are independently selected from $C_1$-$C_{12}$ hydrocarbons, preferably, $C_1$-$C_{12}$ alkyl, alkenyl or aryl, or H, more preferably, $C_1$-$C_{10}$ alkyl, or H, most preferably, $C_1$-$C_6$ alkyl or H, especially, methyl or H;
X is O;
n is an integer from 1 to 100, preferably, 1 to 10, more preferably 1 to 5, especially, 1-3;
and m is 1;
in the presence of a suitable catalyst, and optionally in the presence of methanol.

In a particularly preferred embodiment the compound of formula I is derived from formaldehyde in the presence of methanol and/or water. In such a case, the compound of formula I may be defined as a suitable source of formaldehyde.

For the avoidance of doubt, a suitable source of formaldehyde includes any equilibrium composition which may provide a source of formaldehyde. Examples of such include but are not restricted to methylal (1,1 dimethoxymethane), polyoxymethylenes —$(CH_2$—$O)_i$— wherein i=1 to 100 formalin (formaldehyde, methanol, water) and other equilibrium compositions such as a mixture of formaldehyde, methanol and methyl propionate.

Typically, the polyoxymethylenes are higher formals of formaldehyde and methanol $CH_3$—O—$(CH_2$—$O)_i$—$CH_3$ ("formal-i"), wherein i=1 to 100, preferably, 1-5, especially 1-3, or other polyoxymethylenes with at least one non methyl terminal group. Therefore, the source of formaldehyde may also be a polyoxymethylene of formula $R^{31}$—O—(CH2-O—$)_i R^{32}$, where $R^{31}$ and $R^{32}$ may be the same or different groups and at least one is selected from a $C_2$-$C_{10}$ alkyl group, for instance $R^{31}$=isobutyl and $R^{32}$=methyl.

Preferably, the suitable source of formaldehyde is selected from 1,1 dimethoxymethane, higher formals of formaldehyde and methanol, $CH_3$—O—$(CH_2$—$O)_i$—$CH_3$ where i=2, formalin or a mixture comprising formaldehyde, methanol and methyl propionate.

Preferably, by the term formalin is meant a mixture of formaldehyde:methanol:water in the ratio 25 to 65%: 0.01 to 25%: 25 to 70% by weight. More preferably, by the term formalin is meant a mixture of formaldehyde:methanol:water in the ratio 30 to 60%: 0.03 to 20%: 35 to 60% by weight. Most preferably, by the term formalin is meant a mixture of formaldehyde:methanol:water in the ratio 35 to 55%: 0.05 to 18%: 42 to 53% by weight.

Preferably, the mixture comprising formaldehyde, methanol and methyl propionate contains less than 5% water by weight. More preferably, the mixture comprising formaldehyde, methanol and methyl propionate contains less than 1% water by weight. Most preferably, the mixture comprising formaldehyde, methanol and methyl propionate contains 0.1 to 0.5% water by weight.

Suitable catalysts for the catalytic conversion of methyl propionate (MEP) to MMA using formaldehyde are known to the skilled person. One known catalyst is a basic catalyst such as an alkali metal catalyst on a support, for instance, silica which may include other metals and metal compounds. A suitable silica is a porous high surface area silica. The surface area of the silica may be at least 30 m² g⁻¹. The preferred alkali metal is caesium. The alkali metal may be present at a level 1-10% by weight of catalysts. The catalyst may contain other metals such as magnesium, aluminium, hafnium, boron and/or zirconium. The amount of other metal is variable but good results can be obtained when the other metal is present in such amount that the catalyst contains a total of 0.25 to 2 gram atoms of said modifier element per 100 moles of silica.

Other suitable catalysts include mixed metal oxides $(M^1_wM^2_xO_y)$ wherein $M^1$ is at least one metal selected from group 3 or 4 in the 4th to 6$^{th}$ periods of the periodic table, group 13 in the 3$^{rd}$ to 5$^{th}$ periods of the periodic table, or the remaining elements in the lanthanide series (namely, scandium, yttrium, the lanthanide elements, titanium, zirconium, hafnium; aluminium, gallium, indium) and $M^2$ is at least one metal selected from group 5 in the 5$^{th}$ or 6$^{th}$ periods of the periodic table or group 15 in the 4$^{th}$ or 5$^{th}$ periods of the periodic table (namely, niobium, tantalum, arsenic and antimony); mixed phosphorus containing metal oxides $(M^1_wM^2_xP_yO_z)$ wherein $M^1$ is a group IIIb metal, preferably aluminium, and $M^2$ is a group IVb metal, preferably silicon; nitrided single metal oxides such as nitride $Ta_2O_5$; nitrided mixed metal oxides $(M^1_wM^2_xN_yO_z)$, wherein $M^1$ is selected from the metals of group 2, 3, 4, 13 (called also IIIA) or 14 (called also IVA) of the periodic table and $M^2$ is selected from the metals of groups 5 or 15 (called also VA); and group II phosphates such as hydroxyapatite and orthophosphates, particularly rod or needle like crystal habits of calcium and strontium hydroxyapatite; all optionally in the presence of a suitable support such as silica or alumina.

The catalytic conversion of methyl propionate (MEP) to MMA or MAA using formaldehyde is typically effected at an elevated temperature, usually in the range 250-400° C. Where the desired product is an ester, the reaction is preferably effected in the presence of the relevant alcohol in order to minimise the formation of the corresponding acid through hydrolysis of the ester. Also for convenience it is often desirable to introduce the formaldehyde in the form of formalin. Hence, for the production of methyl methacrylate, the reaction mixture fed to the catalyst will generally consist of methyl propionate, methanol, formaldehyde and water.

Baeyer-Villiger oxidation refers to the insertion of an oxygen atom into a ketone to form an ester. In asymmetric ketones, this insertion reaction occurs almost exclusively between the carbonyl carbon and the most stable carbonion of the ketone. It is generally known that Baeyer-Villiger oxy-insertion for unsymmetrical ketones has the approximate order of migration of tertiary alkyl>secondary alkyl, aryl>primary alkyl>methyl group (March's Advanced Organic Chemistry: Reactions, Mechanisms and Structure 6$^{th}$ Edition, pg. 1619). Accordingly, Baeyer-Villiger oxidation of 2-butanone would traditionally be associated with the product ethyl acetate. Therefore, Baeyer Villiger oxidation of 2-butanone is not a route that the skilled person would readily choose as a route to methyl methacrylate via methyl propionate. Nevertheless, the inventors have found that certain Baeyer-Villiger monooxygenases can insert an oxygen atom into 2-butanone in an abnormal manner, yielding the unlikely product of methyl propionate.

Surprisingly, this has led to an unusual and novel biological route to methyl methacrylate monomer for the polymer industry via sugar and/or glycerol and/or microbe convertible gas fermentation to an alcohol and its subsequent oxidation to 2-butanone and hence MEP via abnormal Baeyer-Villiger oxidation.

It is known that Baeyer-Villiger oxidative enzymes are common to various organisms including bacteria, plants, animals, archea, and fungi. Baeyer-Villiger oxidative enzymes can catalyse the conversion of ketones to esters. However, those enzymes that are reported are only described as acting in biological systems on ring based ketones (lactones), rather than the straight chain aliphatic ketones. In the few studies where their activity on straight chain aliphatic ketones has been tested, they are reported as having very low activity.

The term 'Baeyer-Villiger monooxygenase' as used herein preferably refers to an enzyme capable of catalysing oxidation reactions belonging to the EC classification group 1.14.13.X and such enzymes generally comprise the following characteristic sequences: two Rossman fold protein sequence motifs (GxGxxG) at the N-terminus and the middle of the protein sequence respectively, and the typical BVMO binding motif FxGxxxHxxxW/[P/D] located in a loop region of the folded protein.

The Baeyer-Villiger monooxygenase may be a wild type enzyme, or a modified enzyme. In addition, the enzyme may be synthetic whether in accordance with the wild type or a modification thereof.

The term 'wild type' as used herein whether with reference to polypeptides such as enzymes, polynucleotides such as genes, organisms, cells, or any other matter refers to the naturally occurring form of said matter.

The term 'modified' as used herein with reference to polypeptides such as enzymes, polynucleotides such as genes, organisms, cells, or any other matter refers to such matter as being different to the wild type.

The term 'microbe convertible gas(es)' as used herein means a gas or gases that can be converted by microbes into a raw feedstock. A suitable gas is a gas rich in CO and a suitable fermentation is described in US 2012/0045807A1 which converts CO to 2,3-butanediol using anaerobic fermentation with Clostridia such as *Clostridium autoethanogenum*, *ljundahlii* and *ragsdalei* in appropriate media and under the conditions known to the skilled person.

Suitable alterations to wild type matter that may produce modified matter include alterations to the genetic material, alterations to the protein material.

Alterations to the genetic material may include any genetic modification known in the art which will render the material different to the wild type.

Examples of such genetic modifications include, but are not limited to: deletions, insertions, substitutions, fusions etc. which may be performed on the polynucleotide/s sequence containing the relevant gene or genes to be modified.

Such genetic modifications within the scope of the present invention may also include any suitable epigenetic modifications. Epigenetic modifications may include any modification that affects the relevant genetic material without modification of the polynucleotide/s sequence containing the relevant gene or genes to be modified. Examples of epigenetic modifications include, but are not limited to; nucleic acid methylation or acetylation, histone modification, paramutation, gene silencing, etc.

Alterations to protein material may include any protein modification known in the art which will render the material different to the wild type.

Examples of such protein modifications include, but are not limited to: cleaving parts of the polypeptide including fragmentation; attaching other biochemically functional groups; changing the chemical nature of an amino acid; changing amino acid residues including conservative and non-conservative substitutions, deletions, insertions etc; changing the bonding of the polypeptide etc; which may be performed on the polypeptide/s sequence which fold(s) to form the relevant protein or proteins to be modified.

Alterations to the structure of said materials may include any structural modification known in the art which will render the structure of genetic or protein material different to the wild type.

Examples of such structural modifications include modifications caused by, but not limited to, the following factors: the interaction with other structures; interactions with solvents; interactions with substrates, products, cofactors, coenzymes, or any other chemical present in a suitable reaction including other polynucleotides or polypeptides; the creation of quaternary protein structures; changing the ambient temperature or pH etc. which may be performed on the structure(s) of the relevant genetic or protein material(s) of interest.

Each of the modifications detailed under the groups of genetic alteration, protein alteration or structural alteration above are given as an exemplification of the wide range of possible modifications known to the skilled man, and are not intended to limit the scope of the present invention.

Preferably the Baeyer-Villiger Monooxygenase (BVMO) enzyme is a wild type enzyme. More preferably the Baeyer-Villiger Monooxygenase (BVMO) enzyme is a wild type enzyme deriving from an organism, wherein the organism may be from any domain including the archea, bacteria or eukarya. Still more preferably the Baeyer-Villiger Monooxygenase (BVMO) enzyme is a wild type enzyme deriving from an organism, wherein the organism is from the kingdom of plants, fungi, archeae or bacteria. Still more preferably the Baeyer-Villiger Monooxygenase (BVMO) enzyme is a wild type enzyme deriving from a bacterium, or a fungus.

Suitable bacterial sources of wild type Baeyer-Villiger Monooxygenase (BVMO) enzymes include, but are not limited to, bacteria from the following bacterial genera; *Acinetobacter, Rhodococcus, Arthrobacter, Brachymonas, Nocardia, Exophiala, Brevibacterium, Gordonia, Novosphingobium, Streptomyces, Thermobifida, Xanthobacter, Mycobacterium, Comamonas, Thermobifida* or *Pseudomonas*. Preferred bacterial sources of wild type Baeyer-Villiger monooxygenase (BVMO) enzymes are bacteria from the following genera: *Acinetobacter* or *Rhodococcus*.

Suitable fungal sources of wild type Baeyer-Villiger Monooxygenase (BVMO) enzymes include, but are not limited to, fungi from the following fungal genera; *Gibberella, Aspergillus, Maganporthe, Cylindrocarpon, Curvularia, Drechslera, Saccharomyces, Candida, Cunninghamella, Cylindrocarpon,* or *Schizosaccharomyces*. Preferred fungal sources of wild type Baeyer-Villiger monooxygenase (BVMO) enzymes are fungi from the following genera: *Gibberella, Aspergillus* or *Magnaporthe*.

Most preferably the Baeyer-Villiger monooxygenase is a wild type enzyme deriving from the bacterial species *Acinetobacter calcoaceticus* NCIMB 9871 or *Rhodococcus jostii* RHA1 or *Rhodococcus* sp. HI-31 or *Xanthobacter flavus*.

The Baeyer-Villiger monooxygenase may be a type I, type II or type O Baeyer-Villiger monooxygenase. Preferably the Baeyer-Villiger monooxygenase is a type I Baeyer-Villiger Monooxygenase. More preferably the Baeyer-Villiger monooxygenase is a type I Baeyer-Villiger monooxygenase selected from one of the following enzyme groups; a cyclohexanone monooxygenases (CHMO) EC number 1.14.13.22 (GenBank: BAA86293.1); a phenylacetone monooxygenases (PAMO) EC number 1.14.13.92 (Swiss-Prot: Q47PU3); a 4-hydroxyacetophenone monooxygenase (HAPMO) EC number 1.14.13.84 (GenBank: AAK54073.1); an acetone monooxygenases (ACMO) (GenBank: BAF43791.1); a methyl ketone monooxygenases (MEKA) (GenBank: ABI15711.1); a cyclopentadecanone monooxygenases (CPDMO) (GenBank: BAE93346.1); a cyclopentanone monooxygenases (CPMO) (GenBank: BAC22652.1); a steroid monooxygenases (STMO) (GenBank: BAA24454.1). Still more preferably the Baeyer-Villiger monooxygenase is a cyclohexanone monooxygenase, a 4-hydroxyacetophenone monooxygenase, a cyclopentadecanone monooxygenase or an acetone monooxygenase, which may be selected from one of the following enzymes: cyclohexanone monooxygenase from *Acinetobacter calcoaceticus* NCIMB 9871, cyclohexanone monooxygenases from *Xanthobacter flavus* (GenBank: CAD10801.1), cyclohexanone monooxygenases from *Rhodococcus* sp. HI-31 (GenBank: BAH56677.1), cyclohexanone monooxygenase from *Brachymonas petroleovorans* (GenBank: AAR99068.1), 4-hydroxyacetophenone monooxygenase (Q93TJ5.1), cyclopentadecanone monooxygenase (GenBank: BAE93346.1), or acetone monooxygenase from *Gordonia* sp. TY-5 (Genbank: BAF43791.1).

Still more preferably, the Baeyer-Villiger monooxygenase is a cyclohexanone monooxygenase, or an acetone monoxygenase, which may be selected from cyclohexanone monooxygenase from *Acinetobacter calcoaceticus* NCIMB 9871, cyclohexanone monooxygenases from *Xanthobacter flavus* (GenBank: CAD10801.1), cyclohexanone monooxygenases from *Rhodococcus* sp. HI-31 (GenBank: BAH56677.1), cyclohexanone monooxygenase from *Brachymonas petroleovorans* (GenBank: AAR99068.1), or acetone monooxygenase from *Gordonia* sp. TY-5 (Genbank: BAF43791.1).

Surprisingly, the inventors have found that cyclohexanone monoxygenases can produce methyl propionate at a high rate with concentrations of only 5 mM 2-butanone substrate.

Therefore, most preferably, the Baeyer-Villiger monooxygenase is cyclohexanone monooxygenase preferably deriving from *Acinetobacter calcoaceticus* NCIMB 9871, *Xanthobacter flavus* (GenBank: CAD10801.1) or *Rhodococcus* sp. HI-31 (GenBank: BAH56677.1).

Most preferably the Baeyer-Villiger monooxygenase is a wild type enzyme deriving from the bacterial species *Acinetobacter calcoaceticus* NCIMB 9871 or *Rhodococcus jostii*

RHA1 or *Rhodococcus* sp. HI-31 or *Xanthobacter flavus* or *Brachymonas petroleovorans*.

Furthermore, the inventors have surprisingly found that 4-hydroxyacetophenone monooxygenase, and cyclopentadecanone monooxygenase can also produce methyl propionate at industrially significant levels.

Therefore, in an alternative preferred embodiment, the Baeyer-Villiger monooxygenase is a 4-hydroxyacetophenone monooxygenase or a cyclopentadecanone monooxygenase. More preferably, a 4-hydroxyacetophenone monooxygenase (Q93TJ5.1) or a cyclopentadecanone monooxygenase (GenBank: BAE93346.1).

Preferably the 4-hydroxyacetophenone monooxygenase derives from *Pseudomonas flourescans*.

Preferably the cyclopentadecanone monooxygenase derives from *Pseudomonas* sp. HI-70. (see UniProt taxonomy database, Taxon identifier 341693, based on the NCBI taxonomy database)

Therefore, most preferably the Baeyer-Villiger monooxygenase enzyme is a 4-hydroxyacetophenone monooxygenase from the bacterial species *Pseudomonas flourescans*, or a cyclopentadecanone monooxygenase from the bacterial species *Pseudomonas* sp. HI-70.

In any case, the Baeyer-Villiger monooxygenase enzyme is preferably selected from one of a cyclohexanone monooxygenase, a 4-hydroxyacetophenone monooxygenase, or a cyclopentadecanone monooxygenase.

Optionally, the Baeyer-Villiger Monoxygenase used in the present invention may be present as a mixture of one or more of the abovementioned Baeyer-Villiger Monoxygenase enzymes. In which case, the Baeyer-Villiger Monooxygenase (BVMO) may be derived from any one or more of the sources described above, in any combination or formulation. For example, the Baeyer-Villiger Monooxygenase (BVMO) may be a mixture of a BVMO enzyme derived from a bacterium and a BVMO enzyme derived from a fungus, where one enzyme may be a modified enzyme and one may be a wild type enzyme.

Alternatively, in a further embodiment, the Baeyer-Villiger Monooxygenase may be present as a modified enzyme. Preferably the modified BVMO enzyme is a genetically modified enzyme wherein the genetic material of the BVMO enzyme has been altered from the wild type. In one embodiment, the genetically modified BVMO enzyme may be a fusion protein which has been constructed from parts of the wild type genetic sequence of one or more of the abovementioned Baeyer-Villiger Monoxygenases so as to create a chimera. Preferred examples of such chimeric BVMOs include, for example: PASTMO (a fusion of PAMO and STMO), or PACHMO (a fusion of PAMO and CHMO) as described by van Beek et al. in Chemical Communications 2012, 48, 3288-3290.

Preferably the Baeyer-Villiger monooxygenase is produced by propagating a host organism which has been transformed with the relevant nucleic acids to express said Baeyer-Villiger monooxygenase in a manner known in the art. Suitable host organisms include, but are not limited to: bacteria, fungi, yeasts, plants, algae, protists, etc.

Preferably the relevant nucleic acids are expressed upon an expression vector within the host organism. Suitable expression vectors include any commercially available vector known in the art, such as, but are not limited to; phage, plasmids, cosmids, phagemid, fosmid, bacterial artificial chromosomes, yeast artificial chromosomes etc.

Suitably the most appropriate vector, method of transformation, and all other associated processes necessary for the expression of a BVMO enzyme in a host organism, as discussed below for bacteria, are adapted for the relevant host organism as known in the art.

Preferably the host organism is a bacterium. Suitably, therefore the expression vector used is any commercially available plasmid, such as, but not limited to: pBR, pUC, pBS, pBE, ColE, pUT, pACYC, pA, pRAS, pTiC, pBPS, pUO, pKH, pWKS, pCD, pCA, pBAD, pBAC, pMAK, pBL, pTA, pCRE, pHT, pJB, pET, pLME, pMD, pTE, pDP, pSR etc. More preferably the expression vector used is one of the following commercially available plasmids; pBAD, pCREor pET.

Optionally, the expression vector may be a modified expression vector which is not commercially available and has been altered such that it is tailored to the particular expression of a BVMO enzyme within a host organism. Accordingly, in a preferred embodiment, the expression vector used is the pCRE2 plasmid, based on the commercial pBAD plasmid for expression of the BVMO enzyme in a host bacterium, as described in Tones Pazmino et al. ChemoBioChem 10:2595-2598 (2009).

Preferably the host bacterium is transformed by any suitable means known in the art, including, but not limited to; microinjection, ultrasound, freeze-thaw methods, microporation or the use of chemically competent cells. More preferably the host bacterium is transformed by electroporation.

Suitable host bacteria include those from the genus; *Streptomyces, Escherichia, Bacillus, Streptococcus, Salmonella, Staphylococcus*, or *Vibrio*. Preferably the host bacterium is selected from the genus *Escherichia*. More preferably the host bacterium is the species *Escherichia coli*. Most preferably the host bacterium is the strain *Escherichia coli* TOP10.

Preferably the relevant nucleic acids expressed upon the expression vector are genetic sequences encoding the Baeyer-Villiger monooxygenase plus any further genetic sequences necessary to effect its expression in a host bacterium as known in the art, such as, but not limited to; promoters, terminators, downstream or upstream effectors, suppressors, activators, enhancers, binding cofactors, initiators, etc.

Preferably the expression vector further comprises genetic sequences encoding at least one expression marker. The expression marker enables the host bacterial cells which have been transformed correctly to be identified. Suitable expression markers include any known in the art, but are not limited to; an antibacterial resistance gene, a pigment producing gene, a pigment inhibiting gene, a metabolic capacity gene, or a metabolic incapacity gene. More preferably the expression marker is an antibacterial resistance gene. Still more preferably the antibacterial resistance gene is an ampicillin resistance gene. Accordingly, only those bacteria able to grow on media containing ampicillin are expressing the vector and have been transformed correctly. Preferably the expression vector further comprises genetic sequences encoding at least one activator. The activator enables the host bacterial cells which have been transformed to be stimulated to produce the BVMO enzyme at the appropriate times by interaction with an inducer substance. Suitable activator-inducer systems include any known in the art, but particularly the ara operon where L-arabinose is the inducer, or the lac operon where the inducer is allolactose or IPTG.

Optionally, the expression vector may further comprise genetic sequences encoding a tag. Preferably the genetic sequences encoding said tag are operable to be continuously transcribed with the genetic sequences encoding the Baeyer Villiger Monooxygenase enzyme, such that the tag forms a fusion protein with the resulting Baeyer Villiger Monooxygenase enzyme. The tag enables the resulting Baeyer Villiger Monooxygenase enzyme to be purified easily from the host bacterial lysate. Suitable tags include any known in the art, but are not limited to; a His-tag, a GST tag, a MBP tag, or an antibody tag.

Preferably the host bacterium is grown by culturing it in, or on, a suitable media under suitable conditions as known in the art, wherein the media may be a broth or a set gel. Preferably the media contains a source of nutrients, a selective component to select for the presence of the expression marker, and an inducer to induce expression of the expression vector in the bacteria, wherein the selective component and the inducer are specific to the expression vector used. Preferably the media is a broth. More preferably the media is Luria-Bertani broth.

The Baeyer-Villiger monooxygenase may be present in the reaction mixture of the above process in any suitable form known in the art, such as but not limited to; a free cell extract, a synthetic enzyme, or contained within the host organism cells, and these may be located within the reaction mixture in any suitable way known in the art, such as but not limited to; in free form in solution, held upon a membrane, or bound to/within a column.

Preferably the BVMO is present in the reaction mixture at a concentration necessary to produce the required amount of methyl propionate capable of being produced at the relative level of dissolved oxygen. Typically, in an industrial situation, about 0.01 to 0.5 moles of $O_2$ per litre per hour are dissolved into the reaction mixture which is capable of giving about 0.01 to 0.5 moles of methyl propionate per litre per hour.

The term 'about' indicates a marginal limit of a maximum of 20% above or below the stated value. Preferably within 10% above or below the stated value.

In one embodiment, the Baeyer-Villiger monooxygenase is present in the reaction mixture as a cell extract from the cell it was expressed in, wherein the cell is preferably the host bacterial cell used to produce the BVMO enzyme. The cell extract may be obtained by any suitable means capable of lysing the host bacterial cells, including, but not limited to; sonication, DNAse/lysozyme treatment, freeze-thaw treatment, or alkaline treatment.

Preferably the cell extract is then treated to remove cellular debris before being used as a source of Baeyer-Villiger monooxygenase in the above process. The cell lysate may be treated by any suitable means known in the art, including, but not limited to; filtration, centrifugation, or purification with salts to obtain a cleared cell extract.

Preferably further components are present in the reaction mixture of the above process in order to allow the Baeyer Villiger Monooxygenase enzyme to function correctly. Preferably the further components are; a buffer or pH stat, NADPH, and optionally an NADPH regenerating agent.

Any suitable buffer may be used in the reaction mixture, suitable buffers include, but are not limited to; Tris-HCl, TAPS, Bicine, Tricine, TAPSO, HEPES, TES, MOPS, PIPES, Cacodylate, SSC, or MES. Preferably the buffer used in the reaction mixture is Tris-HCl.

Alternatively, a pH stat may be used to control the pH of the reaction mixture.

Preferably the buffer or the pH stat maintains the reaction mixture at a suitable pH for the BVMO enzyme to function and/or the host organism comprising said BVMO enzyme to live. Preferably the buffer or the pH stat maintains the reaction mixture at a pH between about pH 6.5 to pH 8.5. More preferably the buffer or the pH stat maintains the reaction mixture at a pH of between about pH 7.3 and 7.7. Still more preferably the buffer or the pH stat maintains the reaction mixture at a pH of about 7.5.

The term 'about' as used with reference to the pH of the reaction mixture indicates a marginal limit of a maximum of 20% above or below the stated value. However, preferably the pH of the reaction mixture is within 10% above or below the stated value.

Preferably the concentration of buffer in the reaction mixture is between about 25 to 100 mM. More preferably the concentration of buffer in the reaction mixture is between about 40 and 60 mM. Still more preferably the concentration of buffer in the reaction mixture is about 50 mM.

The term 'about' as used with reference to the concentration of buffer indicates a marginal limit of a maximum of 20% above or below the stated value. However, preferably the concentration of buffer is within 10% above or below the stated value.

Preferably the NADPH is present in the reaction mixture at a starting molar concentration relative to BVMO such that the BVMO enzyme is saturated with NADPH. Therefore, preferably the NADPH is present in the reaction mixture at a concentration which is at least equal to the concentration of BVMO enzyme.

Preferably in one embodiment, the NADPH is present in the reaction mixture at a starting concentration of between about 50 to 200 µM. More preferably the NADPH is present in the reaction mixture at a starting concentration of between about 90 to 110 µM. Still more preferably the NADPH is present in the reaction mixture at a starting concentration of about 100 uM. The term 'about' as used with reference to the concentration of NADPH indicates a marginal limit of a maximum of 20% above or below the stated value. However, preferably the concentration of NADPH is within 10% above or below the stated value.

Preferably the NADPH regenerating agent is present in the reaction mixture at a concentration of between about 5 to 20 µM. More preferably the NADPH regenerating agent is present in the reaction mixture at a concentration of between about 8 to 12 uM. Still more preferably the NADPH regenerating agent is present in the reaction mixture at a concentration of about 10 uM.

Preferably, if used, the NADPH regenerating agent is present in the reaction mixture at a molar concentration relative to BVMO such that the BVMO is saturated with NADPH. Preferably therefore, the Km of the NADPH regenerating agent, if used, is at least equivalent to the rate of consumption of NADPH by the BVMO.

The term 'about' as used with reference to the concentration of NADPH regenerating agent indicates a marginal limit of a maximum of 20% above or below the stated value. However, preferably the concentration of NADPH regenerating agent is within 10% above or below the stated value.

Any suitable NADPH regenerating agent may be used in the reaction mixture, such as, but not limited to; phosphite dehydrogenase, glucose-6-phosphate dehydrogenase, alcohol dehydrogenase, or formate dehydrogenase. Suitably, the relevant partner substrate to the NADPH regenerating agent is also present within the reaction mixture, such as, but not limited to; glucose, an alcohol, phosphite or formate.

Alternatively, NADPH may be provided into the reaction mixture as a macromolecular cofactor covalently linked to a support, for example a membrane, resin, or gel.

Preferably the partner substrate is present in the reaction mixture at a concentration of between 5 mM to 20 mM, more preferably at a concentration of between about 8 mM to 12 mM, still more preferably at a concentration of about 10 mM.

Preferably the partner substrate is present in the reaction mixture at a molar concentration relative to the NADPH regenerating agent (NADPH regenerating agent: partner substrate) of between about 1:4000 and 1:250. More preferably the partner substrate is present in the reaction mixture at a molar concentration relative to the NADPH regenerating agent of about 1:1000.

The term 'about' as used with reference to the concentration of partner substrate to the NADPH regenerating agent indicates a marginal limit of a maximum of 20% above or below the stated value. However, preferably the concentration of partner substrate to the NADPH regenerating agent is within 10% above or below the stated value.

Suitably, substrate is present in the above reaction mixture in order to start the BVMO conversion of 2-butanone to methyl propionate. Preferably, in such an embodiment, the concentration of 2-butanone substrate present in the above reaction mixture is between about 10 g/L and 200 g/L. More preferably the concentration of 2-butanone substrate present in the above reaction mixture is between about 50 g/L and 130 g/L. Still more preferably the concentration of 2-butanone substrate present in the above reaction mixture is between about 90 g/L and 110 g/L The term 'about' as used with reference to the concentration of substrate indicates a marginal limit of a maximum of 20% above or below the stated value. However, preferably the concentration of substrate is within 10% above or below the stated value. Preferably, in such an embodiment, the concentration of 2-butanone substrate present in the above reaction mixture is at least about 10% by weight of the reaction mixture, more preferably it is between at least about 20% by weight of the reaction mixture, up to about 80% by weight of the reaction mixture.

In an alternative embodiment, the Baeyer-Villiger monooxygenase may be present in the reaction mixture as a synthetic enzyme. In such an embodiment, the synthetic enzyme is synthesised in vitro in a manner known in the art then purified before being used in the reaction mixture. Preferably the reaction mixture comprises the same components as defined in the reaction mixture above at substantially the same concentrations and ratios.

In a further alternative embodiment, the Baeyer-Villiger Monooxygenase may be present in the reaction mixture within the host organism cells, such as bacterial cells. In such an embodiment, the host cells are prepared in a manner known in the art then purified before being used in the reaction mixture. Preferably the reaction mixture comprises buffer and substrate as defined in the reaction mixture above. Preferably the buffer is present at the same concentrations and ratios defined above.

However, preferably, in such an embodiment, the concentration of 2-butanone substrate present in the above reaction mixture is less than the concentration limit which is toxic to the host cells, and which is optimal for uptake of the substrate into the host cells. Preferably, therefore, the concentration of 2-butanone substrate present in the above reaction mixture is between about 0.2 g/L and 50 g/L. More preferably the concentration of 2-butanone substrate present in the above reaction mixture is between about 0.2 g/L and 30 g/L. Still more preferably the concentration of 2-butanone substrate present in the above reaction mixture is between about 0.2 g/L and 20 g/L.

The term 'about' as used with reference to the concentration of substrate indicates a marginal limit of a maximum of 20% above or below the stated value. However, preferably the concentration of substrate is within 10% above or below the stated value.

Preferably, in such an embodiment, the concentration of 2-butanone substrate present in the above reaction mixture is at least about 1% by weight of the reaction mixture, more preferably it is between at least about 2% by weight of the reaction mixture, up to about 20% by weight of the reaction mixture.

Suitably, in such an embodiment, the concentration of BVMO enzyme present in the reaction mixture is determined by the concentration of host cells present in the reaction media. Preferably the concentration of host cells present in the reaction media is between about 1 g/L and 100 g/L. More preferably the concentration of host bacterial cells present in the reaction media is between about 5 g/L and 50 g/L. Still more preferably the concentration of host bacterial cells present in the reaction media is between about 10 g/L and 20 g/L. Typically, the host cells are bacterial cells.

Suitably in such an embodiment, the reaction mixture does not comprise added NADPH or an optional NADPH regenerating agent and partner substrate because they are already present within the host cell biochemistry.

Preferably, regardless of the form of BVMO source used in the reaction mixture, an in situ product removal system is implemented together with a substrate feeding strategy in the reaction process. It has been found that removal of product together with a constant substrate feed can increase product yields to much higher values, as described by Alphand et al. in Trends in Biotechnology Vol. 21 No. 7 Jul. 2003. Any product removal system and any substrate feeding strategy known in the art may be implemented. However, preferably the product removal system and substrate feeding system are implemented using the same technology, for example, by the use of a carrier material which can simultaneously act as a reservoir for substrate and a sink for product. One such technology is the use of Optipore L-493 resin described by Simpson et al. Journal of Molecular Catalysis B Enzyme 16, pp. 101-108

Advantageously, the inventors have further found that the use of certain co-solvents in the reaction mixture can increase the relative and/or absolute level of the methylpropionate product. The term 'absolute level' as used herein refers to the actual percentage value of methyl propionate obtained as a product in solution from the conversion of 2-butanone. The term 'relative level' as used herein refers to the selectivity i.e. the percentage of methyl propionate obtained as a product in solution compared to the alternative product ethyl acetate obtained as a product in solution from the conversion of 2-butanone.

Preferably, therefore, at least one co-solvent is included in the above reaction mixture, suitable co-solvents include, but are not limited to, one of the following: methanol, 2-butanol, tert-butanol, dioxane, acetone or acetonitrile.

Optionally, the role of the co-solvent in the reaction mixture may also be fulfilled by the substrate 2-butanone. Accordingly, excess 2-butanone in addition to that needed for the substrate catalysis may be used.

Surprisingly, an increase in the concentration of substrate, beyond those levels routinely used in such enzymatic conversions, increases the reaction selectivity of the BVMO to produce more abnormal insertions and more methyl propionate relative to the normal ethyl acetate product. Surprisingly, at concentrations in excess of 1000 times molar concentration relative to BVMO, there is an increase in abnormal insertions, formation of the abnormal ester, by the BVMO enzyme such that the ratio of ethyl acetate production to methyl propionate production is reduced. Accordingly, the concentration of co-solvent/substrate is at 1000:1 or greater mol:mol BVMO, more preferably, at 5000:1 or greater mol:mol, most preferably, at 10000:1 or greater mol:mol BVMO. The maximum level will depend on the particular reaction but should be less than that at which selectivity and/or conversion decreases. In any case, it is generally <1000000:1 mol:mol BVMO, most preferably between 25000 and 125000 times the molar concentration of co-solvent/substrate relative to BVMO.

Advantageously, the inventors have found that the use of methanol in particular as a co-solvent greatly increases the relative level of methylpropionate product compared to ethylacetate product, and also greatly increases the absolute level of methylpropionate over and above the increases seen for any other co-solvent.

Accordingly, most preferably the co-solvent used is methanol.

Surprisingly, the use of methanol at increased concentrations in the reaction mixture increases the reaction selectivity of the BVMO to produce more abnormal insertions and more methyl propionate relative to the normal ethyl acetate product.

Preferably, therefore, the ratio of methyl propionate:ethyl acetate production by the BVMO enzyme in the above process is at least 1:5, more preferably at least 1:2, still more preferably at least 1:1.5, most preferably at least 1:0.5.

Surprisingly, the use of methanol at increased concentrations also increases the absolute level of methyl propionate product produced in the above process.

Preferably, therefore, the Baeyer Villiger monoxygenase converts 2-butanone to methyl propionate at an absolute level of at least 2% selectivity in the above process. More preferably the Baeyer Villiger monoxygenase enzyme converts 2-butanone to methyl propionate at an absolute level of at least 5% selectivity. Still more preferably the Baeyer Villiger monoxygenase converts 2-butanone to methyl propionate at an absolute level of at least 9% selectivity.

Preferably the Baeyer Villiger Monooxygenase converts 2-butanone to methyl propionate at a relative level of at least 20%. More preferably the Baeyer Villiger monoxygenase enzyme converts 2-butanone to methyl propionate at a relative level of at least 50%. Still more preferably the Baeyer Villiger monoxygenase enzyme converts 2-butanone to methyl propionate at a relative level of at least 100%.

Methyl propionate is preferably treated to produce methyl methacrylate or derivatives thereof by any suitable known chemical or biochemical process. Preferably the methyl propionate is treated to produce methyl methacrylate or methacrylic acid by reaction with formaldehyde or a suitable source thereof in the presence of a suitable catalyst as described above.

As mentioned above, the process may further comprise the step of formation of 2-butanone from raw feedstocks, wherein the term 'raw feedstocks' includes any base organic chemical capable of being transformed into 2-butanone, such as, but not limited to; 2-butanol, acetoin, 2,3-butandiol, or methylvinylketone.

Therefore, according to one embodiment of a first aspect of the present invention, there is provided a process of producing methyl methacrylate or derivatives thereof comprising the steps of;
(i) formation of 2-butanone from raw feedstocks;
(ii) converting said 2-butanone to methyl propionate using a Baeyer-Villiger monooxygenase; and
(iii) treating the methyl propionate produced to obtain methyl methacrylate or derivatives thereof.

Preferably the step of formation of 2-butanone from raw feedstocks comprises the conversion of 2-butanol to 2-butanone.

Therefore, according to a preferred embodiment of a first aspect of the present invention, there is provided a process of producing methyl methacrylate or derivatives thereof comprising the steps of
(i) formation of 2-butanone from 2-butanol;
(ii) converting said 2-butanone to methyl propionate using a Baeyer-Villiger monooxygenase; and
(iii) treating the methyl propionate produced to obtain methyl methacrylate or derivatives thereof.

This conversion of 2-butanol to 2-butanone may be catalysed either chemically or enzymatically. Preferably this conversion is catalysed enzymatically. More preferably this conversion is catalysed by a dehydrogenase enzyme. Still more preferably this conversion is catalysed by an alcohol dehydrogenase enzyme under EC group number 1.1.1.X.

Preferably the alcohol dehydrogenase enzyme is an enzyme capable of dehydrogenating butanol, such as those under EC number 1.1.1.1 More preferably the alcohol dehydrogenase an enzyme capable of dehydrogenating butanol derived from an organism. Still more preferably the dehydrogenase capable of dehydrogenating butanol may derive from, for example, one of the following organisms: *Acetobacter pasteurianus, Acinetobacter calcoaceticus, Aeropyrum pernix, Anastrepha* species, *Avena sativa, Brassica napus, Brevibacterium* species, *Camellia sanensis, Candida* species, *Chlamydomonas moewussi, Citrillus lanatus, Corynebacterium glutamicum, Coturnix coturnix, Cricetulus griseus, Crocus sativas, Cucumis melo, Desulfovibrio gigas, Devosia riboflavine, Dipodascus capitatus, Drosophila* species, *Emericulla nidulans, Entamoeba histolytica, Escherichia coli, Euglena* species, *Flavobacterium frigidimaris, Gallus gallus, Fragaria ananassa, Geobacillus* species, *Hafnia alvei, Hordeum vulgare, Klebsiella* species, *Kluyveromyces* species, *Leifsoia* species, *Methylobacterium* species, *Neurospora crassa, Oryza sativa, Pseudomonas* species, *Rhodococcus* species, *Saccharomyces* species, *Sulfobulus* species, *Thermoanaerobacter* species, *Thermomicrobium roseum, Thermoplasma acidophilum, Thermus* species, *Triticum* species, *Vicia fabia, Vitis vinifera, Zea mays, Zygosaccharomyces rouxii*, or *Zymomonas mobilis*.

In a particularly preferred embodiment, the alcohol dehydrogenase enzyme is a thermostable NADP-dependent alcohol dehydrogenase under EC group number 1.1.1.2. More preferably the alcohol dehydrogenase enzyme is a thermostable NADP-dependent alcohol dehydrogenase from a thermophilic microbe. Still more preferably the alcohol dehydrogenase enzyme is a thermostable NADP-dependent alcohol dehydrogenase from a thermophilic bacterium. Most preferably the alcohol dehydrogenase enzyme is a thermostable NADP-dependent alcohol dehydrogenase from the bacterium *Thermoanaerobacter brockii* (Swiss-Prot: P14941.1).

Preferably the alcohol dehydrogenase enzyme is co-expressed with the BVMO enzyme in a host organism, which is preferably a bacterium. Preferably, therefore, the expression vector discussed above, further comprises genetic sequences encoding the alcohol dehydrogenase enzyme and any further genetic sequences necessary to effect its expression in a host bacterium, such as, but not limited to; promoters, terminators, downstream or upstream effectors, suppressors, activators, enhancers, binding cofactors, etc.

Alternatively, the alcohol dehydrogenase enzyme may be expressed in a host organism upon a different vector from the BVMO enzyme.

Advantageously, it has been found that the alcohol dehydrogenase is also operable to provide an NADPH regenerating system. During its conversion of 2-butanol to 2-butanone, the alcohol dehydrogenase will oxidise 2-butanol thereby providing electrons that are readily available to regenerate NADPH from NADP+ produced by the BVMO during its conversion of 2-butanone to methyl propionate. When both the alcohol dehydrogenase and the BVMO enzymes are coexpressed, closed circle NADPH regeneration can occur without the need for external input of an NADPH regeneration agent to the system. Thereby improving the stochiometry and solving a potential redox bottleneck created by the BVMO catalysis, this allows the reactions of 2-butanol to 2-butanone to methyl propionate to proceed faster and more efficiently as a true cascade reaction.

Preferably this step is carried out in a reaction mixture comprising at least the alcohol dehydrogenase enzyme, and the substrate 2-butanol, in a manner that is known in the art and under conditions which are optimal to the given enzyme. Such conditions including optimal concentrations and ratios being deducible through routine processes within the knowledge of the skilled man.

Alternatively, the step of formation of 2-butanone from raw feedstocks may comprise the conversion of acetoin to 2,3-butanediol, and the conversion of 2,3-butanediol to 2-butanone.

Therefore, according to a further preferred embodiment of a first aspect of the present invention, there is provided a process of producing methyl methacrylate or derivatives thereof comprising the steps of;
formation of 2,3-butanediol from acetoin;
(ii) formation of 2-butanone from 2,3-butandiol;
(iii) converting said 2-butanone to methyl propionate using a Baeyer-Villiger monooxygenase; and
(iv) treating the methyl propionate produced to obtain methyl methacrylate or derivatives thereof.

These conversions may be catalysed either chemically or enzymatically. Preferably these conversions are catalysed enzymatically.

More preferably the conversion of acetoin to 2,3-butandiol is catalysed by a dehydrogenase enzyme and the conversion of 2,3-butandiol to 2-butanone is catalysed by a dehydratase enzyme. Still more preferably the conversion of acetoin to 2,3-butandiol is catalysed by an alcohol dehydrogenase enzyme under EC group number 1.1.1.X, and the conversion of 2,3-butandiol to 2-butanone is catalysed by a diol dehydratase enzyme under EC group number 4.2.1.X.

Preferably the alcohol dehydrogenase enzyme is an enzyme capable of dehydrogenating acetoin, such as those under EC group number 1.1.1.4 or 1.1.1.76. More preferably the alcohol dehydrogenase enzyme is an enzyme capable of dehydrogenating acetoin deriving from an organism. Still more preferably the alcohol dehyrogenase capable of dehydrogenating acetoin dehydrogenase may derive from, for example, one of the following organisms: *Aeromonas hydrophila, Bacillus* species, *Brevibacillus* species, *Enterobacter* species, *Enterococcus* species, *Gluconobacter oxydans, Klebsiella* species, *Lactococcus lactis, Micrococcus* species, *Paenibacillus polymyxa, Paracoccus denitrificans, Pseudomonas* species, *Pyrococcus furiosus, Saccharomyces* species, *Corynebacterium glutamicum*, or *Seratia marcescens*.

Preferably the diol dehydratase enzyme is a diol dehydratase enzyme capable of dehydrating 2,3-butandiol, such as those under EC group number 4.2.1.28. More preferably the diol dehydratase capable of dehydrating 2,3-butandiol is a diol dehydratase deriving from an organism. Still more preferably the diol dehydratase capable of dehydrating 2,3-butandiol may derive, for example, from one of the following organisms: *Acetobacterium* species, *Citrobacter freundii, Clostridium glycolicum, Flavobacterium* species, *Klebsiella* species, *Lactobacillus* species, *Salmonella* species, or *Propionibacterium freudenreichii*.

Preferably the alcohol dehydrogenase enzyme and the diol dehydratase enzyme are co-expressed with the BVMO enzyme in a host organism, which is preferably a bacterium. Preferably, therefore, the expression vector discussed above, further comprises genetic sequences encoding the alcohol dehydrogenase enzyme and the diol dehydratase enzyme and any further genetic sequences necessary to effect its expression in a host bacterium, such as, but not limited to; promoters, terminators, downstream or upstream effectors, suppressors, activators, enhancers, binding cofactors, etc.

Alternatively, the alcohol dehydrogenase enzyme and/or the diol dehydratase enzyme may be expressed in a host organism upon a different vector from the BVMO enzyme.

Preferably this step is carried out in a reaction mixture comprising at least the alcohol dehyrogenase enzyme, the diol dehydratase enzyme and the substrate acetoin in a manner that is known in the art and under conditions which are optimal to the given enzymes. Such conditions including optimal concentrations and ratios being deducible through routine processes within the knowledge of the skilled man.

Alternatively, the step of formation of 2-butanone from raw feedstocks may comprise the conversion of acetoin to methylvinylketone, and the conversion of methylvinylketone to 2-butanone.

Therefore, according to a further preferred embodiment of a first aspect of the present invention, there is provided a process of producing methyl methacrylate or derivatives thereof comprising the steps of
(i) formation of methylvinylketone from acetoin;
(ii) formation of 2-butanone from methylvinylketone;
(iii) converting said 2-butanone to methyl propionate using a Baeyer-Villiger monooxygenase; and
(iv) treating the methyl propionate produced to obtain methyl methacrylate or derivatives thereof.

These conversions may be catalysed either chemically or enzymatically. Preferably these conversions are catalysed enzymatically.

More preferably the conversion of acetoin to methylvinylketone is catalysed by an alcohol dehydratase enzyme and the conversion of methylvinylketone to 2-butanone is catalysed by an enone reductase. Still more preferably the conversion of acetoin to methylvinylketone is catalysed by an alcohol dehydratase enzyme under EC group number 4.2.1.X, and the conversion of methylvinylketone to 2-butanone is catalysed by an enone reductase under EC group number 1.1.1.X or 1.3.1.X.

Preferably the alcohol dehydratase enzyme is an enzyme capable of dehydrating acetoin, such as those enzymes under EC group number 4.2.1.53 or 4.2.1.43 or 4.2.1.3 or those described by Jianfeng et al. in Chemical Communications, 2010, 46, 8588-8590. More preferably the alcohol dehydratase enzyme is an enzyme capable of dehydrating acetoin deriving from an organism. Still more preferably the alcohol dehydratase capable of dehydrating acetoin may derive from, for example, one of the following organisms: *Pseudomonas* species, *Elizabethkingia meningoseptica, Azospirillium brasilense, Herbaspirillium seropedicae, Pelomonas saccharophila, Rhizobium* species, *Sulfolobus* species, *Acer pseudoplatanus, Arabidopsis thaliana, Aspergillus niger, Azotobacter vinelandii, Bacillus* species, *Bacte-*

*roides fragilis, Bos taurus, Caenorhabditis elegans, Corynebacterium glutamicum, Drosophila* species, *Escherichia coli, Crassostrea virginica, Cucurbita* species, *Mycobacterium tuberculosis, Mus musculus, Nicotiana* species, *Plasmodium falciparum, Rattus* species, *Saccharomyces* species, *Salmonella* species, *Streptomyces* species, *Zea mays* or *Xanthomonas campestris,*

Preferably the enone reductase enzyme is an enzyme capable of reducing methylvinylketone such as those enzymes under EC group number 1.1.1.54 or 1.3.1.31 or those described by Yamamoto et al. in U.S. Pat. No. 6,780,967. More preferably the enone reductase enzyme is an enzyme capable of reducing methylvinylketone deriving from an organism. Still more preferably the enone reductase capable of reducing methylvinylketone may derive from, for example, one of the following organisms: *Clostridium tyrobutyricum, Clostridium kluyveri, Saccharomyces pombe, Nicotania tabacum, Euglena gracilis, Astasia longa, Klyveromyces lactis, Pseudomonas putida, Escherichia coli* or *Rattus* species.

Preferably the enone reductase enzyme and the alcohol dehydratase enzyme are co-expressed with the BVMO enzyme in a host organism, which is preferably a bacterium. Preferably, therefore, the expression vector discussed above, further comprises genetic sequences encoding the alcohol dehydrogenase enzyme and any further genetic sequences necessary to effect its expression in a host bacterium, such as, but not limited to; promoters, terminators, downstream or upstream effectors, suppressors, activators, enhancers, binding cofactors, etc. Alternatively, the enone reductase and/or the alcohol dehydratase enzyme may be expressed in a host organism upon a different vector from the BVMO enzyme.

Preferably this step is carried out in a reaction mixture comprising at least the enone reductase, alcohol dehydratase enzyme, and the substrate acetoin in a manner that is known in the art and under conditions which are optimal to the given enzymes. Such conditions including optimal concentrations and ratios being deducible through routine processes within the knowledge of the skilled man.

As mentioned above, the process may further comprise the step of fermentation of sugars and/or glycerol and/or microbe convertible gases (such as gases rich in CO and/or $CO_2$) to produce raw feedstocks, wherein the term 'raw feedstocks' include any base organic chemical capable of being transformed into 2-butanone, such as, but not limited to; 2-butanol, acetoin, 2,3-butandiol, or methylvinylketone.

Therefore, according to a further embodiment of a first aspect of the present invention, there is provided a process of producing methyl methacrylate or derivatives thereof comprising the steps of;

(i) fermentation of said sugars and/or glycerol and/or microbe convertible gas to produce raw feedstocks;
(ii) formation of 2-butanone from said raw feedstocks;
(iii) converting said 2-butanone to methyl propionate using a Baeyer-Villiger monooxygenase; and
(iv) treating the methyl propionate produced to obtain methyl methacrylate or derivatives thereof.

Preferably the step of fermentation of sugars and/or glycerol and/or microbe convertible gas to produce raw feedstocks comprises fermentation of sugars and/or glycerol and/or microbe convertible gas to produce 2-butanol.

Therefore, according to a further preferred embodiment of a first aspect of the present invention, there is provided a process of producing methyl methacrylate or derivatives thereof comprising the steps of;

fermentation of sugars and/or glycerol and/or microbe convertible gas to produce 2-butanol;
(ii) formation of 2-butanone from 2-butanol;
(iii) converting said 2-butanone to methyl propionate using a Baeyer-Villiger monooxygenase; and
(iv) treating the methyl propionate produced to obtain methyl methacrylate or derivatives thereof.

Preferably, the fermentation of sugars to 2-butanol is catalysed enzymatically. Processes to perform such fermentation are well known in the art, for example, one such process is described in U.S. Pat. No. 5,753,474, or more recently in PCT application number WO2007/130521. In particular, WO2007/130521 discloses four different pathways from the fermentation of biomass, specifically biomass which is a source of fermentable sugars (see list given on pages 59 and 60), which may be used to produce to 2-butanol on an industrial scale (see FIG. 1 of WO2007/130521).

Suitably the fermenting organism is a carbohydrate utilising organism, therefore the sugars available in the biomass are taken up by natural routes and enter the Embden Myerhof-Parnas Pathway (EMP) pathway, the Entner-Douderoff pathway, and the pentose phosphate pathway which are the central metabolic routes providing energy from carbohydrates for growth. Key to these pathways is the intermediate glyceraldehyde-3-phosphate which is converted to pyruvate during respiration to produce energy. Pyruvate is therefore a readily available naturally occurring chemical created in most carbohydrate utilising organisms.

As described in WO2007/130521, pyruvate can be converted to 2-butanol by using a modified carbohydrate utilising organism which has been genetically engineered to contain the appropriate Biochemistry to conduct any of the above four pathways in FIG. 1. For example, pathway 1 may be used, pathway 1 contains the conversion steps a, b, c, d, e and f.

Step (a) comprises the conversion of two molecules of pyruvate to alpha-acetolactate. Preferably, enzymes under EC group number EC 2.2.1.6 are used to catalyse this reaction, such as, for example: an acetolactate synthase or an acetohydroxy acid synthase. More preferably, the enzyme used to catalyse this reaction is an acetolactate synthase. Still more preferably, it is one of the following acetolactate synthases: *Bacillus subtilis* (GenBank: AAA22222 NCBI L04470), *Klebsiella terrigena* (GenBank: AAA25055 NCBI L04507) or *Klebisella Pneumoniae* (GenBank: AAA25079 NCBI M73842).

Step (b) comprises the conversion of alpha-acetolactone to acetoin. Preferably, enzymes under EC group number EC 4.1.1.5 are used to catalyse this reaction, such as, for example: an acetolactate decarboxylase. More preferably, it is one of the following acetolactate decarboxylases: *Bacillus subtilis* (GenBank: AAA22223 NCBI L04470), *Klebsiella terrigena* (GenBank: AAA25054 NCBI L04507) or *Klebisella Pneumoniae* (GenBank: AAU43774 NCBI AY22056).

Step (c) comprises the conversion of acetoin to 3-amino-2-butanol. Preferably enzymes under the general group of transaminases or reductive aminases are used to catalyse this reaction, for example: a pyridoxal phosphate dependent transaminase which can be considered as an acetoin aminase. More preferably the pyridoxal phosphate dependent transaminase is an amino:pyruvate transaminase. Still more preferably, it is an amino:pyruvate transaminase from *Vibrio Fluvialis* JS17 (see example 13 of WO2007/130521).

Step (d) comprises the conversion of 3-amino-2-butanol to 3-amino-2-butanol 0-phosphate. Preferably enzymes under the general group of aminoalcohol kinases are used to catalyse this reaction, for example: an ATP dependent ethanolamine kinase under EC number 2.7.1.82 which can be considered as an aminobutanol kinase. More preferably, the ATP dependent ethanolamine kinase originates from a species of the *Pseudomonas* or *Erwinia* genera. Still more preferably, it is an ATP dependent ethanolamine kinase from *Erwinia carotovera* strain SCRI1043 (see example 14 of WO2007/130521).

Step (e) comprises the conversion of 3-amino-2-butanol 0-phosphate to 2-butanone. Preferably enzymes under the general group of aminoalcohol phosphate phospho-lyases are used to catalyse this reaction, such as, for example: a pyroxidal phosphate dependent phosphoethanolamine phospho-lyase which can be considered as an aminobutanol phosphate phospho-lyase. More preferably, the pyroxidal phosphate dependent phosphoethanolamine phospho-lyase originates from a species of the *Pseudomonas* or *Erwinia* genera. Still more preferably, it is a pyroxidal phosphate dependent phosphoethanolamine phospho-lyase from *Erwinia* carotovera strain SCRI1043 (see example 15 of WO2007/130521).

Step (f) comprises the conversion of 2-butanone to 2-butanol. Preferably enzymes under EC group number EC 1.1.1.2 are used to catalyse this reaction, such as, for example a butanol dehydrogenase, or a cyclohexanone dehydrogenase. More preferably, the enzyme used to catalyse this reaction is a butanol dehydrogenase. Still more preferably, the enzyme used to catalyse this reaction is one of the following butanol dehydrogenases: *Pyrococcus furiosus* (GenBank: AAC25556 NCBI AF013169) or *Escherichia coli* (GenBank: NP_417484 NCBI NC_000913). WO2007/130521 further describes the techniques and procedures known in the art which can be used to construct plasmid vectors encoding the various enzymes such that a pathway can be expressed in a host organism, as a demonstration, pathway 3 is fully exemplified.

Furthermore, related patent application WO2007/146377 describes various butanol tolerant organisms which may be used in such a process for the industrial production of 2-butanol, specifically organisms of the *Lactobacillus* genus. Particularly advantageous butanol tolerant species were identified as *Lactobacillus plantarum* PN0510, *Lactobacillus plantarum* (PN0511), *Lactobacillus plantarum* (PN0512) and *Lactobacillus arizonensis* PN0514. In a particularly preferred embodiment of the present invention, at least one of these specific butanol tolerant species is used as the host organism for expressing any one of the above pathways described by WO2007/130521.

Preferably the fermentation of glycerol to 2-butanol is catalysed enzymatically. Processes to perform such fermentation are well known in the art, for example, one such process is described in U.S. Pat. No. 8,119,844B2, and more recently in US patent application number US2011/207191.

In particular, U.S. Pat. No. 8,119,844 discloses the anaerobic fermentation of commercial glycerol or a glycerol containing by-product from industrial waste to produce butanol using the organism *Clostridium pasteurianum*.

U.S. Pat. No. 8,119,844 describes that the anaerobic fermentation is conducted in a bioreactor as known in the art from, for example, Biebel (Journal of Industrial Microbiology and Biotechnology (2001) 27, pp. 18-26) with the wild type *Clostridium pasteurianum* bacterium which is able to convert glycerol substrates into 2-butanol via natural pathways.

Accordingly, preferably the bacterium used in the step of converting glycerol to 2-butanol is a wild type bacterium, more preferably a wild type bacterium of the genus *Clostridium*, still more preferably a wild type bacterium of the species *Clostridium pasteurianum* DSMZ 525.

Optionally, the bacterium used in the step of converting glycerol to 2-butanol may be modified such that its ability to perform such a conversion is enhanced or altered in an advantageous manner by relevant techniques known in the art.

Preferably the glycerol substrate is derived from by-products of industrial waste such that the overall ecological impact or fossil fuel usage of the process of the present invention is minimised. Suitable sources of such waste glycerol include, but are not limited to: biodiesel production, fat saponification, alcoholic beverage production, palm oil production or oleochemical processes. Preferably, the glycerol substrate is derived from biodiesel production. Suitably, the bacterium used to convert glycerol to 2-butanol is fermented with a supply of the glycerol substrate and the 2-butanol product is isolated from the fermentation media. Any appropriate fermentation technique may be used as discussed in U.S. Pat. No. 8,119,844. However, preferably the fermentation media is prepared as described in the example of U.S. Pat. No. 8,119,844, and preferably the fermentation technique is extrapolated to industrial situations from the example given in U.S. Pat. No. 8,119,844, and preferably the isolation of butanol product is carried out as described in columns 10 and 11 of U.S. Pat. No. 8,119,844.

Optionally acetate may be present in enhance the production of 2-butanol from glycerol, and optionally methanol may be removed from the glycerol substrate to enhance the production of 2-butanol from glycerol. Preferably, acetate is present in the fermentation media at a concentration of at least 1 g/L. Preferably the concentration of methanol in the glycerol substrate is at most 10 g/L. Methods to remove methanol from the glycerol substrate are described in column 8 and the example of 'Glycerol Preparation from Biodiesel Waste' in U.S. Pat. No. 8,119,844.

Preferably the fermentation is performed by one or more organisms. More preferably the fermentation is performed by organisms capable of producing the enzyme or enzymes necessary to convert sugars and/or glycerol and/or microbe convertible gas into 2-butanol. Preferably the fermentation is performed by wild type organisms which naturally express the relevant enzyme or enzymes necessary to convert sugars and/or glycerol and/or microbe convertible gas into 2-butanol. More preferably, therefore, the fermentation is performed by wild type organisms comprising the endogenous genetic sequences encoding the enzyme or enzymes necessary to convert sugars and/or glycerol and/or microbe convertible gas into 2-butanol. Examples of such organisms which are preferably used in the present invention are detailed in the abovementioned references describing such fermentation procedures.

Alternatively, the fermentation may be performed by genetically modified organisms which have been modified to express the enzyme or enzymes necessary to convert sugars and/or glycerol and/or microbe convertible gas into 2-butanol. Preferably, therefore, each of the recombinant organisms comprises an expression vector which in turn comprises exogenous genetic sequences encoding the enzyme or enzymes necessary to convert sugars and/or glycerol and/or microbe convertible gas into 2-butanol, plus any further genetic sequences necessary to effect their expression in the host organism, such as, but not limited to; promoters, terminators, downstream or upstream effectors, suppressors, activators, enhancers, binding cofactors, etc.

Preferably the one or more host organisms used for the fermentation of sugars and/or glycerol and/or microbe convertible gas into 2-butanol are bacteria or fungi. Preferably therefore the host bacteria or fungi further comprise genetic sequences encoding the ability to export the 2-butanol produced out of the bacterial cell into the surrounding media. These genetic sequences may be endogeneous or exogenous. The ability to export 2-butanol to the surrounding media may be conferred by genetic sequences encoding a trans-membrane transport pathway, a targeting pathway to the cell membrane, an excretory pathway to the cell membrane, or may be conferred by a simple diffusion gradient across the cell membrane.

For example, in the case of bacteria, the trans membrane pathway may be any one of the following; a type I, II, III, IV, V, VI transporter present in the membrane of a gram negative bacterium; the Sec or TaT pathway present in the membrane of in gram positive bacteria; the vesicle exocytosis pathway in gram negative bacteria; or the N terminal tag pathway in gram positive bacteria.

However, preferably the 2-butanol product is exported out of the bacterial or fungal cells by simple diffusion.

In a preferred embodiment the organisms used for the fermentation step are *Lactobacillus plantarum, Lactobacillus arizonensis* and/or *Clostridium pasteurianum.*

Alternatively, the step of fermentation of sugars and/or glycerol and/or microbe convertible gas to produce raw feedstocks may comprise the fermentation of sugars and/or glycerol and/or microbe convertible gas to produce acetoin.

Therefore, according to a further preferred embodiment of a first aspect of the present invention, there is provided a process of producing methyl methacrylate or derivatives thereof comprising the steps of;
(i) fermentation of sugars and/or glycerol and/or microbe convertible gas to produce acetoin;
(ii) formation of 2,3-butanediol from acetoin;
(iii) formation of 2-butanone from 2,3-butandiol;
(iv) converting said 2-butanone to methyl propionate using a Baeyer-Villiger monooxygenase; and
(v) treating the methyl propionate produced to obtain methyl methacrylate or derivatives thereof.

Alternatively, according to a further embodiment of a first aspect of the present invention there is provided a process of producing methyl methacrylate or derivatives thereof comprising the steps of
(i) fermentation of sugars and/or glycerol and/or microbe convertible gas to produce acetoin;
(ii) formation of methylvinylketone from acetoin;
(iii) formation of 2-butanone from methylvinylketone;
(iv) converting said 2-butanone to methyl propionate using a Baeyer-Villiger monooxygenase; and
(v) treating the methyl propionate produced to obtain methyl methacrylate or derivatives thereof.

Preferably, the fermentation of sugars to acetoin is catalysed enzymatically. Processes to perform such fermentation are well known in the art, for example, one such process is described by Hespell in Current Microbiology Vol. 32 (1996), pp 291-296, and a further process is also described in European patent number EPO430406B1.

In particular, EPO430406B1 discloses the conversion of sugar sources into high yields of acetoin by the use of a shaking fermentation culture wherein the conversion is performed by a lactic acid bacterium.

EPO430406B1 describes that lactic acid bacteria can produce acetoin at high levels from pyruvic acid sources such as citric acid or glucose. Specifically, that high levels of acetoin can be produced from the aerobic fermentation of a lactic acid bacterium with a sugar source in a shaking fermentation technique with the addition of a metal salt and a source of iron porphyrin.

Accordingly, preferably the bacterium used in the step of converting sugars to acetoin is a wild type bacterium, more preferably a wild type lactic acid bacterium, still more preferably a wild type lactic acid bacterium of the genus *Lactococcus, Leuconostoc,* or *Lactobacillus,* yet more preferably a wild type lactic acid bacterium of the species *Streptococcus lactis* (ATCC 11007), *Lactococcus lactis* (FERM-BP-2805), *Lactobacillus casei* (FERM-BP-2806), *Lactobacillus casei* (ATCC334), or *Leuconostoc cremoris* (ATCC19254).

Optionally, the bacterium used in the step of converting sugars to acetoin may be modified such that its ability to perform such a conversion is enhanced or altered in an advantageous manner by relevant techniques known in the art.

Preferably the sugar substrate is derived from any carbon source that is able to be utilised by the fermenting bacterium. More preferably the sugar substrate is glucose or lactose.

Suitably, the bacterium used to convert sugars to acetoin is fermented with a supply of the sugar substrate and the acetoin product is isolated from the fermentation media. Any appropriate fermentation technique may be used. However, preferably the fermentation media is MRS media, more preferably the MRS media is prepared as described on page 4 line 5 of EPO430406B1 which can be extrapolated to industrial situations. Preferably the fermentation technique used is as described in any of the examples of EPO430406B1 which can also be extrapolated to industrial situations, more preferably the fermentation technique used is that described in example 3 of 0430406B.

Preferably the fermentation of glycerol to acetoin is catalysed enzymatically. Processes to perform such fermentation are well known in the art, for example, one such process is described in the above-mentioned PCT application WO2007/130521, and the much earlier publication by Dobrogosz et al. Journal of Bacteriology vol. 84 (1962) pp. 716-723.

In particular, Dobrogosz et al. demonstrates that knowledge of certain organisms producing acetoin directly from glycerol has existed from as early as 1962. Table 3 shows the significant accumulation of acetoin in the bacterium *Pediococcus pentosaceus.*

Dobrogosz describes that under aerobic fermentation conditions, bacteria from the family Lactobacillaceae (or lactic acid bacteria) can produce acetoin from glycerol substrate via an inherent pathway which proceeds via the key intermediate pyruvic acid (see FIG. 4).

Accordingly, preferably the bacterium used in the step of converting glycerol to acetoin is a wild type bacterium, more preferably a wild type lactic acid bacterium, still more preferably a wild type lactic acid bacterium of the genus *Pediococcus* or *Streptococcus,* yet more preferably a wild type lactic acid bacterium of the species *Pediococcus pentosaceus Az-25-5/Pediococcus cerevisiae,* or *Streptococcus faecalis* B33A/10C1.

Optionally, the bacterium used in the step of converting glycerol to acetoin may be modified such that its ability to perform such a conversion is enhanced or altered in an advantageous manner by relevant techniques known in the art.

Preferably the glycerol substrate is derived from by-products of industrial waste such that the overall ecological impact or fossil fuel usage of the process of the present invention is minimised. Suitable sources of such waste glycerol include, but are not limited to: biodiesel production, fat saponification, alcoholic beverage production, palm oil production or oleochemical processes. Preferably, the glycerol substrate is derived from biodiesel production.

Suitably, the bacterium used to convert glycerol to acetoin is fermented with a supply of the glycerol substrate and the acetoin product is isolated from the fermentation media. Any appropriate fermentation technique may be used. However, preferably the fermentation media is NYE basal media with the addition of glycerol substrate, more preferably the fermentation media is NYE basal media as described on page 717 of Dobrogosz with the addition of at least 0.163M glycerol as described in table 3 of Dobrogosz. Preferably the fermentation method used is as described on page 717 of Dobrogosz which can be extrapolated to industrial conditions, wherein only glycerol is present in the NYE media and glucose is not added, suitably aerobiosis is maintained in order to allow growth on the glycerol substrate. Preferably the fermentation is conducted in a batch type arrangement wherein each batch fermentation is carried out for a period of between 24 and 48 hours.

Preferably the fermentation is performed by one or more organisms. More preferably the fermentation is performed by organisms capable of producing the enzyme or enzymes necessary to convert sugars and/or glycerol and/or microbe convertible gas into acetoin. Preferably the fermentation is performed by wild type organisms which naturally express the relevant enzyme or enzymes necessary to convert sugars and/or glycerol and/or microbe convertible gas into acetoin.

More preferably, therefore, the fermentation is performed by wild type organisms comprising the endogenous genetic sequences encoding the enzyme or enzymes necessary to convert sugars and/or glycerol and/or microbe convertible gas into acetoin. Examples of such organisms which are preferably used in the present invention are detailed in the abovementioned references describing such fermentation procedures.

Alternatively, the fermentation may be performed by genetically modified organisms which have been modified to express the enzyme or enzymes necessary to convert sugars and/or glycerol and/or microbe convertible gas into acetoin. Preferably, therefore, each of the recombinant organisms comprises an expression vector which in turn comprises exogenous genetic sequences encoding the enzyme or enzymes necessary to convert sugars and/or glycerol and/or microbe convertible gas into acetoin, plus any further genetic sequences necessary to effect their expression in the host organism, such as, but not limited to; promoters, terminators, downstream or upstream effectors, suppressors, activators, enhancers, binding cofactors, etc.

Preferably the one or more host organisms used for the fermentation of sugars and/or glycerol and/or microbe convertible gas into acetoin are bacteria or fungi. Preferably therefore the host bacteria or fungi further comprise genetic sequences encoding the ability to export the acetoin produced out of the bacterial cell into the surrounding media. These genetic sequences may be endogeneous or exogenous. The ability to export acetoin to the surrounding media may be conferred by genetic sequences encoding a trans-membrane transport pathway, an excretory pathway to the cell membrane, a targeting pathway to the cell membrane, or may be conferred simply by a diffusion gradient across the cell membrane.

For example, in the case of bacteria, the trans membrane pathways may be any one of the following; a type I, II, III, IV, V, VI transporter present in the membrane of a gram negative bacterium; the Sec or TaT pathway present in the membrane of in gram positive bacteria; the vesicle exocytosis pathway in gram negative bacteria; or the N terminal tag pathway in gram positive bacteria.

However, preferably the acetoin product is exported out of the bacterial or fungal cells by simple diffusion.

In a preferred embodiment the organisms used for the fermentation step are *Lactococcus lactis* and/or *Pediococcus pentosaceous*.

Preferably the sugars used in the fermentation are naturally occurring monosaccharides or disaccharides. Such sugars include, but are not limited to; glucose, fucose, arabinose, ribose, rubulose, allose, altrose, galactose, xylose, fructose, gulose, lyxose, mannose, rhamnose, threose, talose, iodose, sucrose, lactose, lactulose, maltose, trehalose, cellubiose, kojibiose, nigerose, isomaltose, sophorose, laminaribiose, gentiobiose, turanose, maltulose, palatinose, gentiobiulose, mannobiose, melibiose, rutinose, rutinulose, or xylobiose. More preferably the sugars are glucose or maltose. Still more preferably the sugars are glucose, particularly D-glucose.

Alternatively, the sugars used in the fermentation may be provided as naturally occurring polysaccharides, which are then able to be hydrolysed by the fermenting organisms or other additional enzymes to produce the above monosaccharides and disaccharides. Suitable polysaccharides include, but are not limited to: cellulose, amylose, amylopectin, glycogen, arabinoxylan, chitin, pectin etc.

Preferably the fermentation by the organism is conducted anaerobically or microaerobically.

Suitable anaerobic fermentation techniques include those generally known in the art, such as, but not limited to; submerged, surface, semisolid or solid state fermentation. Preferably the fermentation technique used is submerged fermentation because of its ease in automation and therefore its higher efficiency.

Preferably the fermentation by the organism is conducted in a suitable fermentation broth as known in the art. Preferably the fermentation broth comprises; the sugars and/or glycerol and/or microbe convertible gas mixed with water, the organism, rich media or minimal media, plus additional components such as, but not limited to; a nitrogen source such as ammonia solution; mineral salts such as calcium, magnesium, zinc and copper; and trace elements such as selenium, boron, iron, manganese, phosphorous and sulphur; a chelating agent such as EDTA; ferrocyanide; charcoal; cation exchange resins; an antifoaming agent such as stearyl alcohol, cotton seed oil, linseed oil, olive oil, castor oil, silicones or sulphonates; and methanol.

Preferably the sugars and/or glycerol and/or microbe convertible gas substrates are fed into the fermentation broth over the course of the fermentation in order to avoid substrate inhibition of the enzymatic processes. Preferably the concentration of the sugars and/or glycerol within the fermentation broth is maintained at least at about 25 g/L. More preferably the concentration of the sugars and/or glycerol within the fermentation broth is maintained at between about 25 to 125 g/L. Preferably the sugars and/or glycerol are maintained between these levels by the use of a constant feed of substrate into the fermentation broth wherein the feed concentration is at least enough to keep the majority of the host organisms alive, but not enough to inhibit the product formation.

The microbe convertible gas may be fed into the fermentation substrate at a level of 0.1-15 mol/L·hr, more preferably, at a level of 0.2-5 mol/L·hr, most preferably, 0.3-1 mol/L·hr.

The fermentations and BVMO catalysed reactions of the present invention may be continuous or batch, preferably, a continuous process is used.

The term 'about' as used with reference to the concentration of sugars and/or glycerol and/or microbe convertible gas indicates a marginal limit of a maximum of 20% above or below the stated value. However, preferably the concentration of sugars and/or glycerol and/or microbe convertible gas is within 10% above or below the stated value.

Preferably the products 2-butanol or acetoin produced from the fermentation broth are removed in situ in order to avoid product inhibition of the enzymatic processes. Preferably therefore the concentration of 2-butanol and/or acetoin in the fermentation broth is kept below the level at which it is able to inhibit the fermentation process, preferably this is below about 50 g/L, more preferably below about 25 g/L, still more preferably below about 10 g/L.

The term 'about' as used with reference to the concentration of 2-butanol and/or acetoin indicates a marginal limit of a maximum of 20% above or below the stated value. However, preferably the concentration of 2-butanol and/or acetoin is within 10% above or below the stated value.

Preferably the nitrogen source is carefully controlled. Preferably the nitrogen source is ammonium solution and preferably it is present in the broth at a concentration of about 0-4 g/L. The term 'about' as used with reference to the concentration of nitrogen source indicates a marginal limit of a maximum of 20% above or below the stated value. However, preferably the concentration of nitrogen source is within 10% above or below the stated value.

Preferably the broth is held in a container of substantial size for industrial purposes. The container may be a tank in the range of 40 to 200 cubic metres or a larger fermentor in the range of 200 to 900 cubic metres capacity.

Preferably the fermentation broth is kept aseptic to stop any foreign microorganism growth.

Preferably the fermentation is carried out at an optimum temperature for maximising the amount of the desired product yield from the organisms. Preferably the fermentation is carried out at a temperature of between about 20 and 50° C., preferably between about 20 to 35° C., most preferably between about 28-32° C.

The term 'about' as used with reference to the temperature indicates a marginal limit of a maximum of 10% above or below the stated value. However, preferably the temperature is within 5% above or below the stated value.

Preferably the fermentation is carried out at an optimum pH for bacterial metabolism 6.5 to pH 8.5. More preferably the buffer maintains the reaction mixture at a pH of between about pH 7.3 and 7.7. Still more preferably the buffer maintains the reaction mixture at a pH of about 7.5.The term 'about' as used with reference to the pH indicates a marginal limit of a maximum of 10% above or below the stated value. However, preferably the pH is within 5% above or below the stated value.

Preferably the fermentation broth is agitated; preferably the fermentation broth is agitated vigorously, Agitation allows the sugar substrates to circulate around the organisms evenly and increases the uptake of sugars and/or glycerol and/or microbe convertible gas into the organisms for conversion to the desired product. Agitation may be achieved by any suitable means known in the art, for example; air lift techniques, baffles, Rushton blade or disc turbines, open turbine impellers, or marine impellers.

As mentioned above, the process may further comprise the step of obtaining sugars and/or glycerol and/or microbe convertible gas from biomass, wherein the term 'biomass' is defined herein as plant or animal matter either alive or previously alive and it may be considered to be waste matter or matter intended for the use as described in the present invention.

Therefore, according to a further embodiment of a first aspect of the present invention, there is provided a process of producing methyl methacrylate or derivatives thereof comprising the steps of;

(i) obtaining sugars and/or glycerol and/or microbe convertible gas from biomass;

(ii) fermentation of said sugars or glycerol to produce raw feedstocks;

(iii) formation of 2-butanone from said raw feedstocks;

(iv) converting said 2-butanone to methyl propionate using a Baeyer-Villiger monooxygenase; and (v) treating the methyl propionate produced to obtain methyl methacrylate or derivatives thereof.

Preferably the biomass used comprises a high amount of carbohydrates, particularly preferable are carbohydrates which are sources of glucose such as, but not limited to; starch, cellulose, glycogen, arabinoxylan, chitin, or pectin.

Alternatively, the biomass used comprises a high amount of fats, particularly preferably are fats or oils which are sources of glycerol, specifically triglycerides. Suitable triglycerides include any oil or fat which is readily available from a plant or animal source. Examples of such oils and fats include: palm oil, linseed oil, rapeseed oil, lard, butter, herring oil, coconut oil, vegetable oil, sunflower oil, castor oil, soybean oil, olive oil, coca butter, ghee, blubber etc.

The biomass may be composed of one or more different biomass sources. Examples of suitable biomass sources are as follows; virgin wood, energy crops, agricultural residues, food waste and industrial waste or co-products.

Virgin wood biomass sources may include but are not limited to; wood chips; bark; brash; logs; sawdust; wood pellets or briquettes.

Energy crop biomass sources may include but are not limited to; short rotation coppices or forestry; non-woody grasses such as miscanthus, hemp switchgrass, reeds or rye; agricultural crops such as sugar, starch or oil crops; or aquatic plants such as micro or macroalgae and weeds.

Agricultural residues may include but are not limited to; husks; straw; corn stover; flour; grains; poultry litter; manure; slurry; or silage.

Food wastes may include but are not limited to; peel/skin; shells; husks; cores; pips/stones; inedible parts of animals or fish; pulp from juice and oil extraction; spent grains or hops from brewing; domestic kitchen waste; lard or oils or fats.

Industrial wastes may include but are not limited to; untreated wood including pallets, treated wood, wood composites including MDF/OSD, wood laminates, paper pulp/shreddings/waste; textiles including fibre/yarn/effluent; or sewage sludge.

In one preferred embodiment where sugars are desirable, preferably the biomass used is one or a mixture of different lignocellulosic sources. More preferably the biomass used is one or a mixture of lignocellulosic energy crops. Still more preferably the lignocellulosic energy crops used are high in carbohydrates derived from basic sugars such as glucose, or maltose, yet relatively easy to grow at a high rate such as short rotation grasses. Most preferably the biomass used is miscanthus grass.

In another preferred embodiment where glycerol is desirable, preferably the biomass used is one or a mixture of triglyceride sources. More preferably the biomass used is one or more of a mixture of oils or fats. Still more preferably, the oils or fats used are easily sourced from animal and/or vegetable waste. Most preferably the biomass used is palm oil.

Optionally, a mixed biomass source of any of the above listed biomass may be used such that sugars and glycerol are produced together.

Preferably the sugars and/or glycerol and/or microbe convertible gas are obtained from biomass by the generation of a hydrolysate from raw biomass. Preferably the hydrolysate contains various sugars and/or glycerol and/or microbe convertible gas and other by-products or cellular debris. Preferably the hydrolysate undergoes various purification steps before being used as a sugar/glycerol/gas substrate for fermentation, such purification steps include but are not limited to; filtration, centrifugation, and chemical cleaning.

Preferably the sugars contained in the hydrolysate obtained from the biomass are naturally occurring monosaccharides or disaccharides. Such sugars include, but are not limited to; glucose, fucose, arabinose, ribose, rubulose, allose, altrose, galactose, xylose, fructose, gulose, lyxose, mannose, rhamnose, threose, talose, iodose, sucrose, lactose, lactulose, maltose, trehalose, cellubiose, kojibiose, nigerose, isomaltose, sophorose, laminaribiose, gentiobiose, turanose, maltulose, palatinose, gentiobiulose, mannobiose, melibiose, rutinose, rutinulose, or xylobiose.

More preferably the sugars are glucose or maltose. Still more preferably the sugars are glucose, particularly D-glucose.

Preferably the hydrolysate is generated from raw biomass by processes such as, but not limited to; mechanical shredding, grinding, crushing, extruding, chemical treatments such as acid/base activity, steaming, or hydrolysis in order to release the sugars and/or glycerol from the carbohydrates and triglycerides respectively. This may be particularly necessary for woody sources of biomass where the large biopolymers of cellulose and lignin must be broken down to reach the simple sugars. Once the hydrolysate has been isolated and neutralised it is preferably then mixed with water, rich media or minimal media to produce the basic form of the fermentation broth.

Most preferably, the hydrolysate is always subjected to deionisation to remove any trace heavy metals which may act as enzymatic inhibitors to the organisms to be used in the fermentation step.

Alternatively, the hydrolysate may be generated from biomass at the same time as the fermentation step of the above process, rather than before, such as is known by the term 'SSF' meaning 'simultaneous saccharification and fermentation'.

According to a particularly preferred embodiment of a first aspect of the present invention, there is provided a process of producing methyl methacrylate or derivatives thereof comprising the steps of;
  (i) obtaining glucose and/or glycerol and/or microbe convertible gas from biomass;
  (ii) fermentation of said glucose and/or glycerol and/or microbe convertible gas to 2-butanol;
  (iii) converting said 2-butanol to 2-butanone;
  (iv) converting said 2-butanone to methyl propionate using a Baeyer-Villiger monooxygenase; and
  (v) treating the methyl propionate produced to obtain methyl methacrylate or derivatives thereof.

According to a second aspect of the present invention there is provided a method of preparing polymers or copolymers of methyl methacrylate or derivatives thereof comprising the steps of:
  (i) preparation of methyl methacrylate or derivatives thereof in accordance with the first aspect of the present invention;
  (ii) polymerisation of the methyl methacrylate prepared in (i), optionally with one or more comonomers, to produce polymers or copolymers thereof.

Advantageously, such polymers will have an appreciable portion if not all of the monomer residues derived from a renewable biomass source other than fossil fuels.

In any case, preferred comonomers include for example, monoethylenically unsaturated carboxylic acids and dicarboxylic acids and their derivatives, such as esters, amides and anhydrides.

Particularly preferred comonomers are acrylic acid, methyl acrylate, ethyl acrylate, propyl acrylate, n-butyl acrylate, iso-butyl acrylate, t-butyl acrylate, 2-ethylhexyl acrylate, hydroxyethyl acrylate, iso-bornyl acrylate, methacrylic acid, methyl methacrylate, ethyl methacrylate, propyl methacrylate, n-butyl methacrylate, iso-butyl methacrylate, t-butyl methacrylate, 2-ethylhexyl methacrylate, hydroxyethyl methacrylate, lauryl methacrylate, glycidyl methacrylate, hydroxypropyl methacrylate, iso-bornyl methacrylate, dimethylaminoethyl methacrylate, tripropyleneglycol diacrylate, styrene, α-methyl styrene, vinyl acetate, isocyanates including toluene diisocyanate and p,p'-methylene diphenyl diisocyanate, acrylonitrile, butadiene, butadiene and styrene (MBS) and ABS subject to any of the above comonomers not being the monomer selected from methacrylic acid or a methacrylic acid ester in (i) or (ii) above in any given copolymerisation of the said acid monomer in (i) or a said ester monomer in (ii) with one or more of the comonomers.

It is of course also possible to use mixtures of different comonomers. The comonomers themselves may or may not be prepared by the same process as the monomers from (i) above. According to a third aspect of the present invention there is provided a polymethylmethacrylate (PMMA) homopolymer or copolymer formed from the method according to the second aspect of the present invention.

Advantageously the present invention provides a process for the production of MMA and derivatives thereof from biological sources by the use of a Baeyer Villiger Monooxygenase enzyme to catalyse the abnormal conversion of the aliphatic ketone 2-butanone to methyl propionate at an industrially applicable level.

All of the features contained herein may be combined with any of the above aspects, in any combination which allows the formation of 2-butanone for conversion to Methyl propionate using a BVMO enzyme.

DETAILED DESCRIPTION

It is to be understood by a person having ordinary skill in the art that the present discussion is a description of exemplary embodiments only and is not intended as limiting the broader aspects of the present invention. The following example is provided to further illustrate the invention and is not to be construed to unduly limit the scope of the invention. For a better understanding of the invention, and to show how embodiments of the same may be carried into effect, reference will now be made, by way of example, to the following figures and examples in which:—

FIG. 1 shows the conversion of different concentrations of 2-butanone by 5 µM CHMO.

EXAMPLE 1

BVMO Conversion of 2-Butanone to Methyl Propionate

Chemicals and Enzymes

All chemicals were of analytical grade and obtained from Sigma Aldrich. Cyclohexanone monoxygenase from *Acinetobacter* NCIMB 9871 (CHMO, EC 1.14.13.22) was expressed and purified fused to the N-terminus of a thermostable phosphite dehydrogenase (PTDH, EC 1.20.1.1) for cofactor regeneration, as described above.

Biocatalysis Protocol

Transformations were performed in 15 ml pyrex tubes. Reaction volumes (1 ml) contained 5 mM 2-butanone, 100 uM NADPH, 10 mM $Na_2HPO_3$ and 5 µM CHMO in 50 mM Tris-HCl, pH 7.5. Mixtures were incubated at 24° C. under orbital shaking (200 rpm). To determine conversion, 1 ml reaction volume was extracted with 0.5 nil 1-octanol containing 0.1% mesitylene (1,3,5-trimethylbenzene) as internal standard. Samples were extracted by vortexing for 1 min, followed by a centrifugation step (5000 rpm) for 10 min. The organic layer was removed, dried with $MgSO_4$ and placed in a gas chromatography (GC) vial. GC analysis occurred on a Shimadzu GC instrument fitted with a Heliflex® AT™-5 column (Grace Discovery Sciences). The following temperature profile was used to separate the components: 6 min at 40° C. followed by an increase to 250° C. at 20° C. per minute. Blank reactions without enzyme and with varying amounts of substrate (2-butanone) and product (methyl propionate, ethyl acetate) were carried out under identical circumstances and used to prepare calibration curves for product identification and determination of conversion.

GC Analysis

Table 1 below details the separation time of the compounds by GC following extraction with 1-octanol+0.1% mesitylene from 50 mM Tris-HCl, pH 7.5 (AT-5 column, 5 mM all compounds). All three compounds (1 substrate and 2 products) could reliably be separated by GC.

TABLE 1

Retention time (RT) of compounds after GC separation. 5 mM of all compounds extracted from 50 mM Tris-HCl, pH 7.5 with 1-octanol + 0.1% mesitylene and run on Heliflex AT-5 GC column.

| Compound | RT (min) |
| --- | --- |
| 2-butanone | 3.3 |
| Ethyl acetate | 3.5 |
| Methyl propionate | 3.7 |
| Mesitylene | 10.85 |
| Solvent (1-octanol) | 12.4 |

Synthesis of Methyl Propionate

Table 2 below details the conversion of 2-butanone to ethyl acetate and methyl propionate by CHMO. Co-factor regeneration was carried out by the CHMO fusion partner PTDH (1). Clearly, an industrially significant amount of methyl propionate is formed after 24 hours.

TABLE 2

Conversion of 5 mM 2-butanone by 5 µM CHMO. Reaction in 1 mL 50 mM Tris-HCl, pH 7.5, containing 100 uM NADPH and 10 mM $Na_2HPO_3$ at room temperature for 24 hours. Product identification and determination carried out by GC.

| Product | Conversion (%) |
| --- | --- |
| Ethyl acetate | 40 |
| Methyl propionate | 10 |

Further BVMO enzymes were also tested for the conversion of 2-butanone to methyl propionate using the method stated above for CHMO in table 2. Table 3 shows the results of screening ten BVMO enzymes A-J including CHMO. An industrially significant amount of methyl propionate is formed after 20 hours for the BVMO enzymes, CPDMO and HAPMO.

TABLE 3

Conversion of 100 mM 2-butanone by 5 µM CHMO. Reaction in 1 mL 50 mM Tris-HCl, pH 7.5, containing 100 uM NADPH and 10 mM $Na_2HPO_3$ at 24° C. for 20 hours. Product identification and determination carried out by GC. Example K is a control of 2-butanone with hydrogen peroxide.

| Example | BVMO Enzyme | Methyl Propionate (%) | Ethyl Acetate (%) |
| --- | --- | --- | --- |
| A | PAMO | 0.00 | 10.10 |
| B | PAMO M446G | 0.00 | 1.80 |
| C | HAPMO | 0.14 | 26.10 |
| D | STMO | 0.00 | 4.50 |
| E | CPMO | 0.00 | 7.70 |
| F | CHMO | 6.63 | 13.40 |
| G | CPDMO | 0.02 | 4.40 |
| H | EtaA | 0.00 | 0.00 |
| I | PACHMO | 0.00 | 0.00 |
| J | PASTMO | 0.00 | 5.50 |
| K | 100 mM 2BO + 25 mM $H_2O_2$ | 0.00 | 0.00 |

EXAMPLE 2

Substrate Effect on BVMO Conversion of 2-Butanone to Methyl Propionate

FIG. 1 shows that higher substrate concentrations yield more of the desired, abnormal product. For example: incubation with 5 mM 2-butanone yields an ethyl acetate:methyl propionate ratio of 5:1, and incubation with 1000 mM 2-butanone yields a ratio of 1.5:1

EXAMPLES 3-10

Effect of Co-Solvents on Conversion of 2-Butanone

Various co-solvents were tested for their influence on the ratio of products formed in the reaction of *Acinetobacter* sp. DSM 17874 CHMO with 2-butanone. As in the previous example, 200 mM 2-butanone was observed to have a positive effect on this ratio. In particular, increasing the concentration of 2-butanone results in the formation of more methyl propionate, improving the ethyl acetate:methyl propionate ratio. A number of co-solvents at this concentration (200 mM) were tested. As can be seen from Table 4, 200 mM methanol has a dramatic effect, inverting the ratio completely in favour of methyl propionate. Under these conditions, more methyl propionate is formed than ethyl acetate. The other co-solvents tested also showed a positive effect.

Dioxane, 2-butanol, acetone and acetonitrile all had a significant positive effect on the ratio.

TABLE 4

Effect of different co-solvents on the ratio of products formed in the conversion of 5 mM 2-butanone by *Acinetobacter* CHMO. Conversions were carried out at 24° C. for 18 hrs in 1 ml 50 mM Tris-HCl, pH 7.5. Enzyme concentration was 8 μM.

| Example | Ratio ethyl acetate: methyl propionate | co-solvent (all: 200 mM) |
| --- | --- | --- |
| 3 | 4.77 | none |
| 4 | 1.84 | 2-butanone |
| 5 | 3.33 | dioxane |
| 6 | 4.42 | tert-butanol |
| 7 | 2.71 | 2-butanol |
| 8 | 0.45 | methanol |
| 9 | 2.47 | acetone |
| 10 | 3.84 | acetonitrile |

EXAMPLES 11-13

The effect of co-solvents on the total amount of conversion was also studied, and is highlighted in Table 5. In some cases (dioxane, acetone & acetonitrile) significantly more methyl propionate is formed while less ethyl acetate is formed.

TABLE 5

Effect of different co-solvents on the conversion of 2-butanone to ethyl acetate and methyl propionate by *Acinetobacter* CHMO. The conversion with no co-solvent is set at 100%. The absolute conversion of the reaction with no co-solvent, as determined by calibration curves, is 4.1 mM ethyl acetate and 0.9 mM methyl propionate. Conversions were carried out at 24° C. for 18 hrs in 1 ml 50 mM Tris-HCl, pH 7.5. Enzyme concentration was 8 μM, 2-butanone concentration was 5 mM.

| Example | co-solvent | relative conversion ethyl acetate (%) | relative conversion methyl propionate (%) |
| --- | --- | --- | --- |
|  | none | 100 | 100 |
|  | 2-butanone | * | * |
| 11 | dioxane | 89 | 128 |
| 12 | acetone | 66 | 127 |
| 13 | acetonitrile | 89 | 110 |

*Relative conversion not determined as 2-butanone is the substrate and adding 200 mM obviously does notallow for calculation of sensible relative conversion.

To account for the different extraction efficiency of the substrates and products in the presence of co-solvent, here the calibrations were re-performed with co-solvent to rule out any significant differences.

EXAMPLES 14-16

Purification of a Novel Set of BVMOs & Screening them for the Conversion of 2-Butanone The over-expression and purification of several different BVMOs has been achieved, and is summarized in Table 6. The genes were all cloned into the pCRE3C phosphite dehydrogenase fusion vector and expressed in *E. coli* TOP10. By limiting the culturing temperature to 17° C. significant soluble over-expression was obtained for RmCHMO and XfCHMO. Significant soluble expression was obtained for BpCHMO. The purification protocol involved preparing cell free extracts by sonication in 10 mM sodium phosphate buffer (pH 7.4) with the following additives: 10% glycerol, 0.5 mM dithiothreitol, 100 mM NaCl and 25 mM imidazole.

TABLE 6

Purification of a novel set of BVMOs and the conversion of 2-butanone. CHMO from *Acinetobacter* was included in this table as a reference. Other BVMOs were all expressed and purified as described above. The yields of all purified BVMO proteins ranged between 10 and 20 mg protein per 100 ml culture (Terrific Broth). Conversions were carried out at 24° C. for 18 hrs in 1 ml 50 mM Tris-HCl, pH 7.5 with 100 mM 2-butanone. In this experiment enzyme concentration varied: 8 μM AcCHMO & XfCHMO, 10 μM RmCHMO. As the phosphite concentration used for the conversion was limiting (25 mM) this value is used when determining the conversion (i.e. 100% conversion = 25 mM methyl propionate).

| Example | BVMO | Purified (P) | Forms methyl propionate? (conversion %) |
| --- | --- | --- | --- |
| 14 | AcCHMO | P | y (26%) |
| 15 | RmCHMO | P | y (30%) |
| 16 | XfCHMO | P | y (18%) |

AcCHMO: cyclohexanone monoxygenase from *Acinetobacter* sp. NCIMB 9871; XfCHMO, cyclohexanone monoxygenase from *Xanthobacter flavus*; RmCHMO, cyclohexanone monoxygenase from *Rhodococcus* sp. strain HI-31.

The cell extracts were clarified by centrifugation and incubated with $Ni^{2+}$-sepharose resin for 2 hrs at 4° C. Column material was washed with the same buffer after which the pure protein was eluted as a concentrated yellow fraction (or as a pale band in the case of enriched enzymes) and desalted by gel filtration.

Reassuringly, all CHMOs that were purified displayed similar activity towards 2-butanone, converting it into methyl propionate and ethyl propionate, and all purified CHMOs had the same feature that when the concentration of 2-butanone was increased the ratio of the products formed shifted in favour of methyl propionate. The different CHMOs have similar conversion amounts for methyl propionate, but the ratios of products formed are not identical.

As will be appreciated, some examples show the use of different BVMO enzymes to produce methyl propionate or ethyl acetate. In these examples, particular BVMO enzymes are advantageously shown to produce methyl propionate in favour of ethyl acetate. However, some of the BVMO enzymes tested show no conversion at all, or only conversion to ethyl acetate. Advantageously, the inventors have also discovered the BVMO enzymes which are surprisingly active in the abnormal conversion. In this preferred feature of the invention, the BVMO enzymes that do not show conversion to methyl propionate may be described as comparative examples i.e. Examples A, B, D, E and H-J.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

What is claimed is:

1. A process of producing methyl methacrylate or derivatives thereof comprising the steps of;
   (i) converting 2-butanone to methyl propionate using a Baeyer-Villiger monooxygenase, and
   (ii) treating the methyl propionate produced to obtain methyl methacrylate or derivatives thereof.

2. A process according to claim 1, wherein the methyl propionate is treated to produce methyl methacrylate or methacrylic acid by reaction with formaldehyde or a suitable source thereof in the presence of a suitable catalyst.

3. A process according to claim 1, wherein the Baeyer-Villiger monooxygenase is a wild type enzyme and wherein bacterial sources of the wild type Baeyer-Villiger Monooxygenase enzyme are bacteria from the following bacterial genera; *Acinetobacter, Rhodococcus, Arthrobacter, Brachymonas, Nocardia, Exophiala, Brevibacterium, Gordonia, Novosphingobium, Streptomyces, Therniobda, Xanthobacter, Mycobacterium, Comamonas, Thermobifidar* or *Pseudomonas*.

4. A process according to claim 1, wherein the Baeyer-Villiger monooxygenase is a wild type enzyme deriving from the bacterial species *Acinetobacter calcoaceticus* NCIMB 9871 or *Rhodococcus jostii* RHA1 or *Rhodococcus* sp. HI-31 or *Xanthobacter flavus* or Brachymonas petroleovorans.

5. A process according to claim 1, wherein the Baeyer-Villiger monooxygenase is a type I, type II or type O Baeyer-Villiger monooxygenase.

6. A process according to claim 1, wherein the Baeyer-Villiger monooxygenase is a type I Baeyer-Villiger monooxygenase selected from one of the following enzyme groups: a cyclohexanone monooxygenases (CHMO) EC number 1.14.13.22; a phenylacetone monooxygenases (PAMO) EC number 1.14.13.92; a 4-hydroxyacetophenone monooxygenase (HAPMO) EC number 1.14.13.84; an acetone monooxygenases (ACMO); a methyl ketone monooxygenases (MEKA); a cyclopentadecanone monooxygenases (CPDMO); a cyclopentanone monooxygenases (CPMO); a steroid monooxygenases (STMO).

7. A process according to claim 1, wherein the Baeyer-Villiger monooxygenase is a cyclohexanone monoxygenase, a 4-hydroxyacetophenone monoxygenase, a cyclopentadecanone monooxygenase or an acetone monoxygenase, selected from one of the following enzymes: cyclohexanone monooxygenase from *Acinetobacter calcoaceticus* NCIMB 9871, cyclohexanone monooxygenases from *Xanthobacter flavus*, cyclohexanone monooxygenases from *Rhodococcus* sp. HI-31, cyclohexanone monooxygenase from Brachymonas petroleovorans, 4-hydroxyacetophenone monoxygenase, cyclopentadecanone monooxygenase, or acetone monooxygenase from *Gordonia* sp. TY-5.

8. A process according to claim 1, wherein the Baeyer-Villiger monooxygenase is a cyclohexanone monooxygenase, or an acetone monooxygenase, selected from: cyclohexanone monooxygenase from *Acinetobacter calcoaceticus* NCIMB 9871, cyclohexanone monooxygenases from *Xanthobacter flavus*, cyclohexanone monooxygenases from *Rhodococcus* sp. HI-31, cyclohexanone monooxygenase from Brachymonas petroleovorans, or acetone monooxygenase from *Gordonia* sp. TY-5.

9. A process according to claim 1, wherein the Baeyer-Villiger monooxygenase is selected from a cyclohexanone monoxygenase, a 4-hydroxyacetophenone monooxygenase, or a cyclopentadecanone monooxygenase.

10. A process according to claim 1, wherein the Baeyer-Villiger monooxygenase is a cyclohexanone monooxygenase.

11. A process according to claim 1, wherein the Baeyer-Villiger monooxygenase is cyclohexanone monooxygenase deriving from *Acinetobacter calcoaceticus* NCIMB 9871, *Xanthobacter flavus* or *Rhodococcus* sp. HI-31.

12. A process according to claim 1, wherein the Baeyer-Villiger monooxygenase is a 4-hydroxyacetophenone monooxygenase deriving from *Pseudomonas flourescans*.

13. A process according to claim 1, wherein the Baeyer-Villiger monooxygenase is a cyclopentadecanone monooxygenase deriving from *Pseudomonas* sp. HI-70.

14. A process according to claim 1, wherein at least one co-solvent is included in the reaction mixture of step (i), wherein the co-solvent is selected from one of the following: methanol, 2-butanol, tent-butanol, dioxane, acetone or acetonitrile.

15. A process according to claim 14, wherein the co-solvent used is methanol.

16. A process according to claim 14, wherein the concentration of co-solvent/substrate is at 1000:1 or greater mol: mol of Baeyer-Villiger Monooxygenase.

17. A process according to claim 1, wherein the ratio of methyl propionate: ethyl acetate production by the Baeyer-Villiger Monooxygenase is at least 1:5.

18. A process according to claim 1, wherein the Baeyer Villiger monooxygenase converts 2-butanone to methyl propionate at an absolute level of at least 2% selectivity.

19. A process according to claim 1, wherein the Baeyer Villiger Monooxygenase converts 2-butanone to methyl propionate at a relative level of at least 20%.

20. A method of preparing polymers or copolymers of methyl methacrylate or derivatives thereof comprising the steps of:
   (i) preparation of methyl methacrylate or derivatives thereof in accordance with the process of claim 1;
   (ii) polymerisation of the methyl methacrylate or derivatives thereof prepared in
   (i), optionally with one or more comonomers, to produce polymers or copolymers thereof.

21. A method according to claim 20, wherein the comonomers are monoethylenically unsaturated carboxylic acids and dicarboxylic acids and their derivatives.

22. A method according to claim 20, wherein the comonomers are selected from: acrylic acid, methyl acrylate, ethyl acrylate, propyl acrylate, n-butyl acrylate, iso-butyl acrylate, t-butyl acrylate, 2-ethylhexyl acrylate, hydroxyethyl acrylate, iso-bornyl acrylate, methacrylic acid, methyl methacrylate, ethyl methacrylate, propyl methacrylate, n-butyl methacrylate, iso-butyl methacrylate, t-butyl methacrylate, 2-ethylhexyl methacrylate, hydroxyethyl methacrylate, lauryl methacrylate, glycidyl methacrylate, hydroxypropyl methacrylate, iso-bornyl methacrylate, dimethylaminoethyl methacrylate, tripropyleneglycol diacrylate, styrene, α-methyl styrene, vinyl acetate, isocyanates, acrylonitrile, butadiene, butadiene and styrene (MBS) and ABS.

23. A process according to claim 6, wherein a cyclohexanone monooxygenases (CHMO) is GenBank: BAA86293.1; a phenylacetone monooxygenases (PAMO) is Swiss-Prot: Q47PU3; a 4-hydroxyacetophenone monooxygenase (HAPMO) is GenBank: AAK54073.1; an acetone monooxygenases (ACMO) is GenBank: BAF43791.1; a methyl ketone monooxygenases (MEKA) is GenBank: ABI15711.1; a cyclopentadecanone monooxygenases (CPDMO) is GenBank: BAE93346.1; a cyclopentanone monooxygenases (CPMO) is GenBank: BAC22652.1; and a steroid monooxygenases (STMO) is GenBank: BAA24454.

24. A process according to claim 7, wherein cyclohexanone monooxygenases from *Xanthobacter flavus* is GenBank: CAD10801.1, cyclohexanone monooxygenases from *Rhodococcus* sp. HI-31 is GenBank: BAH56677.1, cyclohexanone monoxygenase from *Brachymonas petroleovorans* is GenBank: AAR99068.1, 4-hydroxyacetophenone monooxygenase is Q93TJ5.1, cyclopentadecanone monooxygenase is GenBank: BAE93346.1, and acetone monooxygenase from *Gordonia* sp. TY-5 is Genbank: BAF43791.1.

25. A process according to claim 8, cyclohexanone monooxygenases from *Xanthobacter flavus* is GenBank: CAD10801.1, cyclohexanone monooxygenases from *Rhodococcus* sp. HI-31 is GenBank: BAH56677.1, cyclohexanone monoxygenase from *Brachymonas petroleovorans* is GenBank: AAR99068.1, and acetone monooxygenase from *Gordonia* sp. TY-5 is Genbank: BAF43791.1.

26. A process according to claim 11, wherein the cyclohexanone monooxygenase deriving from *Xanthobacter flavus* is GenBank: CAD10801.1 and the cyclohexanone monooxygenase deriving from *Rhodococcus* sp. HI-31 is GenBank: BAH56677.1.

27. A method according to claim 21, wherein the derivatives are esters, amides or anhydrides.

28. A method according to claim 22, wherein the isocyanates are toluene diisocyanate or p,p'-methylene diphenyl diisocyanate.

* * * * *